(12) United States Patent
Grinstaff et al.

(10) Patent No.: US 6,288,221 B1
(45) Date of Patent: Sep. 11, 2001

(54) METHODS OF SYNTHESIS OF HALOGEN BASE-MODIFIED OLIGONUCLEOTIDES AND SUBSEQUENT LABELING WITH A METAL-CATALYZED REACTION

(75) Inventors: Mark W. Grinstaff; Amy E. Beilstein; Shoeb I. Khan, all of Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/377,612

(22) Filed: Aug. 19, 1999

Related U.S. Application Data
(60) Provisional application No. 60/097,327, filed on Aug. 20, 1998.

(51) Int. Cl.$^7$ .................................................. C07H 21/00
(52) U.S. Cl. ............................. 536/25.3; 422/131; 435/6; 536/25.32
(58) Field of Search ............................. 536/25.3, 25.32; 435/6; 422/50, 68.1, 131

(56) References Cited

U.S. PATENT DOCUMENTS

| | | |
|---|---|---|
| 4,849,513 | 7/1989 | Smith et al. .......................... 536/27 |
| 5,047,519 | 9/1991 | Hobbs, Jr. et al. .................... 536/23 |
| 5,428,149 | 6/1995 | Eaton ................................. 536/58.55 |
| 5,591,578 | 1/1997 | Meade et al. ............................. 435/6 |
| 5,597,910 | 1/1997 | Gudibande et al. ................. 536/24.3 |
| 5,599,695 | 2/1997 | Pease et al. .......................... 435/91.1 |
| 5,606,045 | 2/1997 | Dandliker et al. ................. 536/25.32 |
| 5,753,788 | 5/1998 | Fodor et al. ......................... 536/22.1 |

FOREIGN PATENT DOCUMENTS 0 229 943   7/1987   (EP) .

OTHER PUBLICATIONS

Ferrer et al., Bioconjugate Chemistry, vol. 8, pp. 757–761, 1997.*

Hurley et al., "Metal–Containing Oligonucleotides: Solid–Phase Synthesis and Luminescence Properties", J. Am. Chem. Soc., 1998, 120, 2194–2195.

Pease et al., "Light–generated Oligonucleotide Arrays for Rapid DNA Sequence Analysis", Proc. Natl. Acad. Sci. USA, vol. 91. pp. 5022–5026, May, 1994.

Hurley et al., "Metal–Containing Oligonucleotides: Solid–Phase Synthesis and Luminescence Properties", J. Am. Chem. Soc., 1998, 120, 2194–2195 Supplementary Information pp. 1–13.

Brun et al., "Photochemistry of Intercalated Quaternary Diazaaromatic Salts", J. Am. Chem. Soc. 1991, 113, 8153–8159.

Winkler et al., "Electron Transfer in Ruthenium–Modified Proteins", Chem, Rev. 1992, 92, 369–379.

Meade et al., "Electron Transfer Through DNA: Site–Specific Modification of Duplex DNA with Ruthenium Donors and Acceptors", Angew, Chem. Int. Ed., Engl. 1995, 34, No. 3.

* cited by examiner

*Primary Examiner*—Ardin H. Marschel
(74) *Attorney, Agent, or Firm*—Nixon & Vanderhye P.C.

(57) ABSTRACT

The present invention provides metal-containing purines, pyrimidines, nucleosides, nucleotides and oligonucleotides; including phosphoramidite and photolabile derivatives thereof, including methods of making and method of using same. The present invention provides a method for detection of nucleic acid sequences via electrochemical or photochemical means.

21 Claims, 22 Drawing Sheets

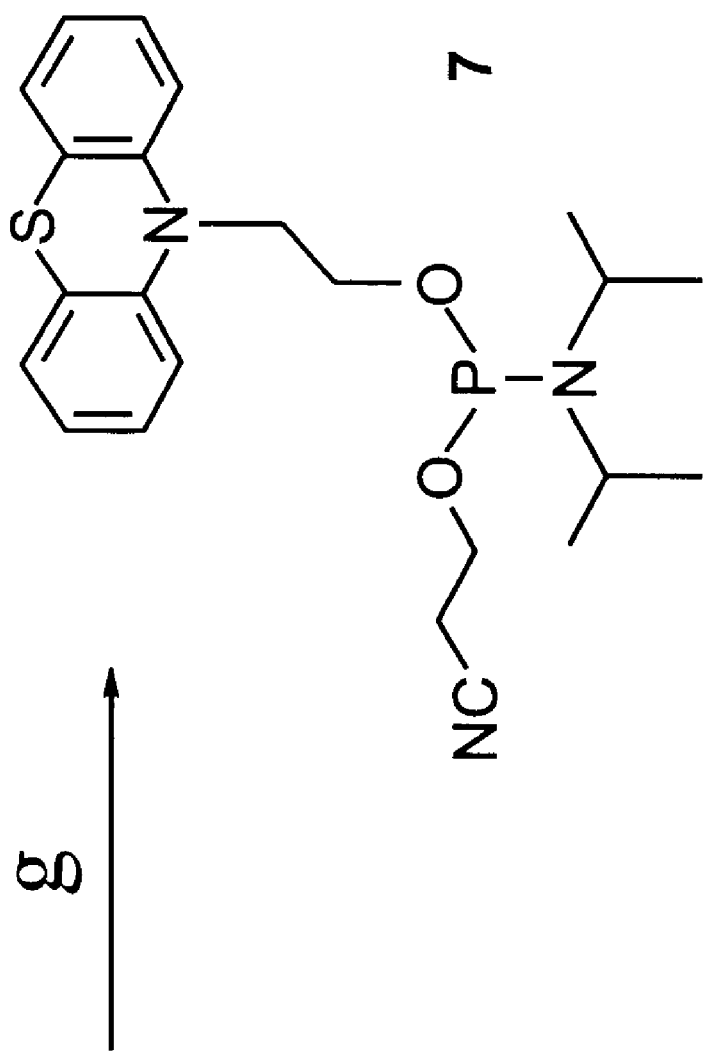
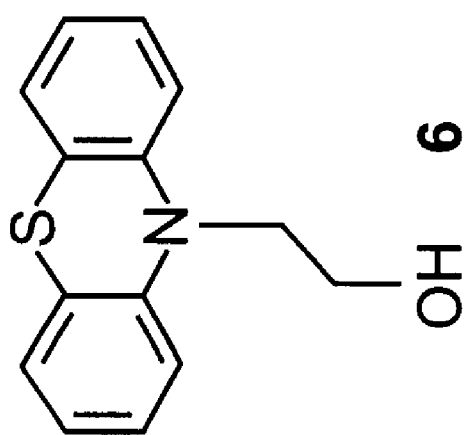
Fig.1B

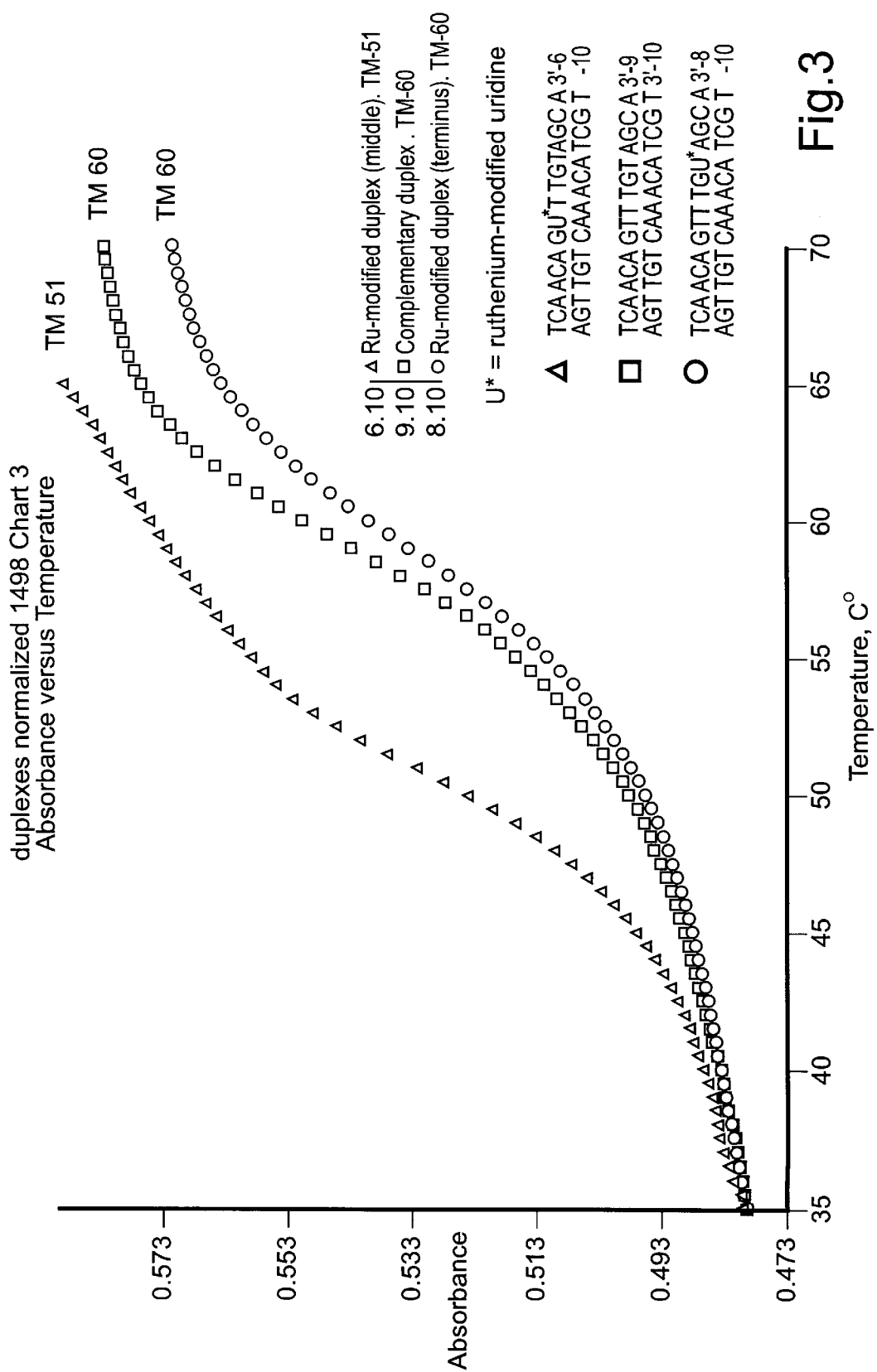

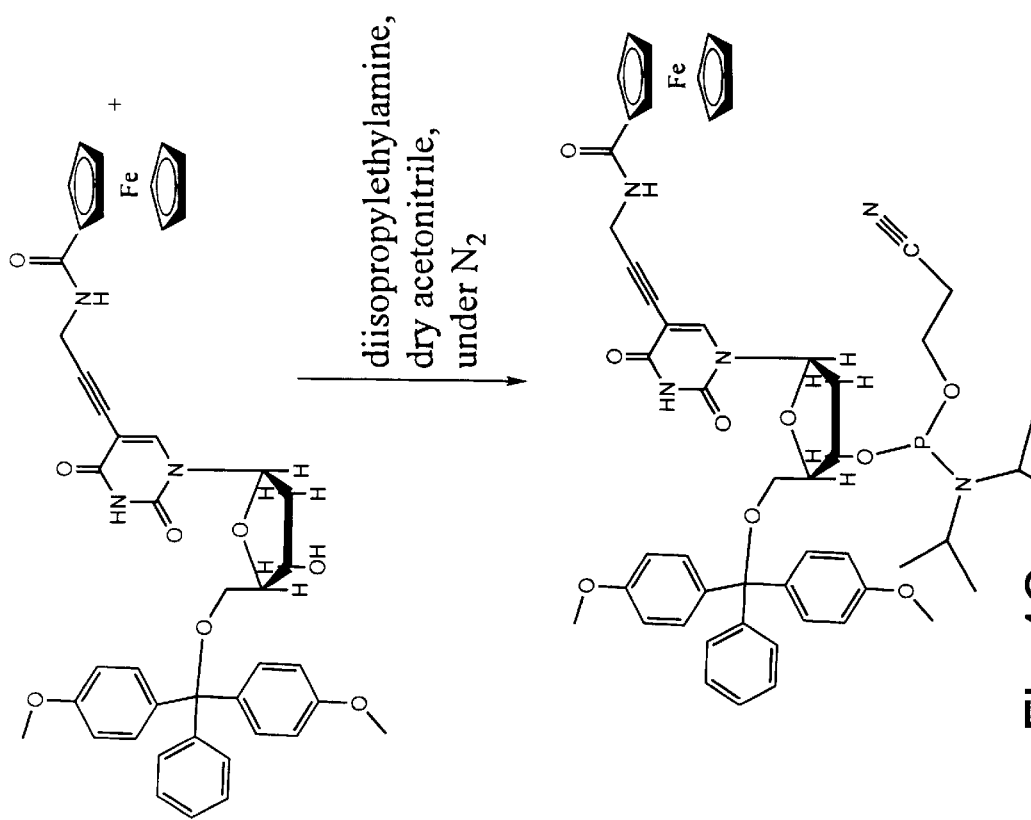
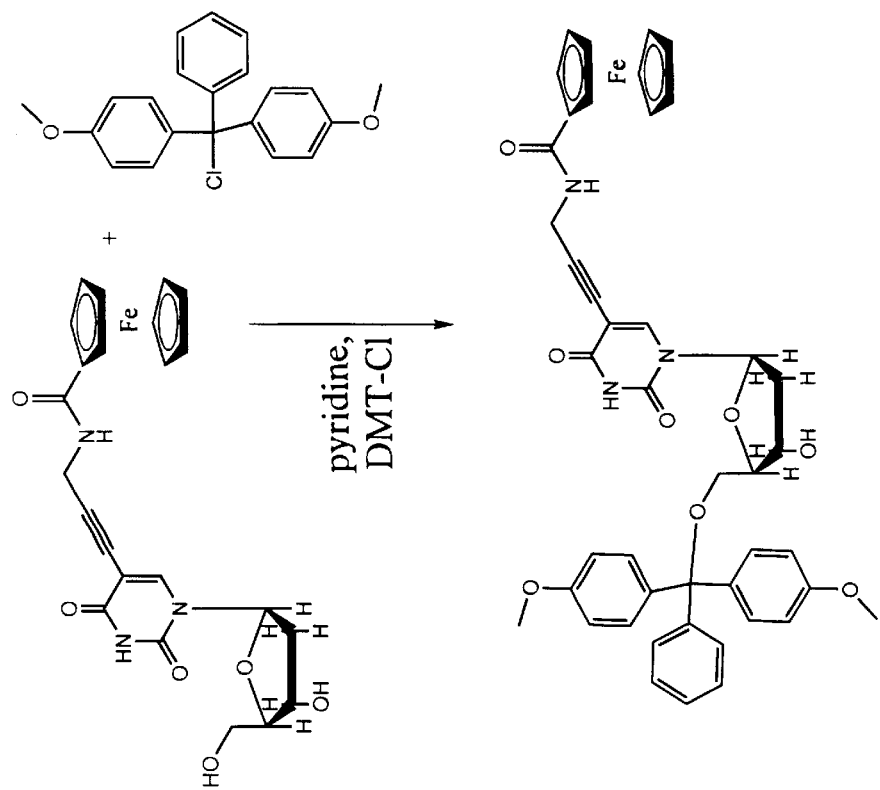
Fig.4C

METHODS OF SYNTHESIS OF HALOGEN BASE-MODIFIED OLIGONUCLEOTIDES AND SUBSEQUENT LABELING WITH A METAL-CATALYZED REACTION

The present application is based on Application No. 60/097,327, filed Aug. 20, 1998, the entire contents of which is incorporated herein by reference.

FIELD OF THE INVENTION

The present invention provides metal-containing purines, pyrimidines, nucleosides, nucleotides and oligonucleotides; including phosphoramidite and photolabile derivatives thereof, including methods of making and methods of using same. The present invention also provides a method for detection of nucleic acid sequences via electrochemical or photochemical means. The present invention provides an improved method of making labeled nucleic acid polymers.

BACKGROUND

Modifying a nucleoside, nucleotide or oligonucleotide with a specific chemical functionality, such as a photo-, redox- or chemically-active metal complex, is of widespread interest for analytical applications (sequencing, hybridization assays), therapeutic uses (anticancer, antiviral pharmaceuticals) and mechanistic studies (electron transfer, structure-function). U. Englisch, D. D. Gauss, Angew. Chem. Int. Ed. Engl. 30 (1991) 613–629; G. H. Keller, M. M. Manak, *DNA Probes*, Stockton Press, New York 1993; P. G. Sammes, and G. Yahioglu, *Natural Product Reports* (1996) 1–28. Synthetic strategies toward these supramolecular bioassemblies focus primarily on post-modification of the synthesized nucleic acid single strand or complementary duplex. A number of researchers, (C. J. Murphy, M. R. Arkin, J. K. Barton, *Science* 262 (1993) 1025–1029; R. E. Holmlin, P. J. Dandliker, J. K. Barton, *Angew, Chem. Int. Ed. Engl.* 36 (1997) 2714–2730 and references therein; D. Magda, R. A. Miller, J. L. Sessler, L. Iverson, *J. Am. Chem. Soc.* 119, (1994) 7439–7440; J. Telser, K. A. Cruickshank. K. S. Schanze, T. L. Netzel. *J. Am Chem. Soc.* 111 (1989) 7221–7226; W. Bannwarth, D. Schmidt. R. L. Stallard. C. Hornung. R. Knorr, F. Müller, *Helv. Chim. Acta* 71 (1988) 2085–2099), have used this strategy to link a metal complex, usually as the activated succinimide ester, to the terminus of the nucleic acid single strand previously modified to contain an alkyl amine. In another approach, an amino- or diimine-modified (e.g., phenanthroline) nucleoside is synthesized, and subsequently reacted with a metal to form the desired complex. G. B. Dreyer, P. B. Dervin, *Biochemistry* 82 (1985) 968–972; C. B. Chen. D. S. Sigman, *J. Am. Chem. Soc.* 110 (1988) 6570–6572; M. Matsumura. M. Endo, M. Komiyama, *J. Chem. Soc., Chem. Commun.* (1994) 2019–2020; J. K. Bashkin. E. I. Frolova. U. Sampath, *J. Am. Chem. Soc.* 116 (1994) 5981–5982; T. J. Meade, J. F. Kayyem. *Angew. Chem. Int. Ed. Engl.* 34 (1995) 352–354. An alternative strategy that offers clear synthetic advantages over the previous systems is to use DNA/RNA solid-phase synthetic methodologies for the site-specific labeling of an oligonucleotide with a transition metal complex. A number of investigations are currently exploring this approach. J. Schliepe, U. Berghoff, B. Lippert, D. Cech, *Angew. Chem. Int. Ed. Engl.* 35 (1996) 646–648; R. Manchanda. S. U. Dunham, S. J. Lippard. *J. Am. Chem. Soc.* 118 (1996) 5144–5145; W. Bannwarth. D. Schmidt, *Tetrahedron Letters* 30 (1989) 1513–1516; E. Meggers. D. Kusch. B. Giese, *Helvetica Chim. Acta* 80 (1997) 640–652; D. J. Hurley. Y. Tor. *J. Am. Chem. Soc.* 120 (1998) 2194–2195).

The present invention provides novel metal-containing purines, pyrimidines, nucleosides and nucleotides, and derivatives thereof, including those which are useful in nucleic acid synthesis, and identification, such as in detection and sequencing. The present invention also provides a new method of labeling purines, pyrimidines, nucleosides, nucleotides and their derivatives during automated or manual synthesis of nucleic acid polymers, such as oligonucleotides, DNA or RNA molecules.

SUMMARY OF THE INVENTION

It is an object of the invention to provide metal-containing purines, pyrimidines, nucleosides, nucleotides, and oligonucleotides, including derivatives and intermediates thereof.

Another object of the present invention is to provide a novel method of synthesizing labeled nucleic acid polymers, such as oligonucleotides, DNA or RNA molecules, preferably by automated methods, which preferably, include use of known iodonucleoside derivatives.

It is another object of the invention to provide a method of making the purine, pyrimidine, nucleoside and nucleotide derivatives of the present invention.

It is yet another object of the invention to provide a method of conducting a polymerase chain reaction or other primer-directed reaction to make and/or detect a nucleic acid of interest in an amplification product of the reaction by incorporating in the reaction product a metal-containing derivative or iodonucleosides, (which may be subsequently labeled) according to the present invention.

It is also an object of the invention to provide a method of detecting a nucleic acid analyte, such as DNA or RNA or dideoxy residues of same, of interest in the product of a polymerase chain reaction or other primer-directed reaction by incorporating at least one purine, pyrimidine, nucleoside or nucleotide derivative of the present invention in the reaction.

Yet another object of the present invention is to provide a solid-phase method of making a nucleic acid polymer, such as an oligonucleotide, which incorporates the metal-containing derivative or halonucleoside, such as iodonucleoside, derivatives of the present invention.

An object of the present invention is to provide a solid surface, including, but not limited to, a bead, plate, or electrode, with a metal-containing derivative of the present invention; and a method for using same.

Specifically, the present invention provides ferrocene; bis(2,2'-bipyridine)(4'-methyl-2,2'-bipyridine-4-carbornyl propargyl amine) ruthenium (11); and bis(2,2'-bipyridine) (4'-methyl-2,2'-bipyridine-4-carbonyl propargyl amine) osmium (II), and corresponding Rh, Cr and Co, nucleoside derivatives. Dimethoxytrityl; 2-cyanoethyl-N,N-diisopropyl-phosphoramidite; phosphotriester; phosphoramidite; and 1-(2-nitro-4-,5-methylene dioxyphenyl) ethyl-choloroformate derivatives are also provided.

The metal complexes described in the present invention are linked to the nucleoside via an amide bond through either the 5, 3 or 2 carbon of the sugar (ribose, deoxyribose or dideoxyribose, for example) or the 5 carbon of a pyrimidine or the 8 carbon of a purine. For example, the amide bond will allow for delocalization of the excited electron on the metal diimine and this will facilitate the electron transfer into the nucleic acid. Preferred amide bonds include alkynylamines.

This is a preferred bonding motif, however other bonding configurations are possible such as, for example, ethers and esters.

BRIEF DESCRIPTION OF THE DRAWINGS

FIGS. 1A and 1B. Synthesis of ruthenium-nucleoside phosphoramidite wherein (a) is propargyl amine HCl, DCC, (dicyclohexylcarbodiimide) HOBt, DIPEA, DMF producing an 82% yield of 2; (b) is $Ru(bp)_2Cl_2$ 70% aq. $C_2H_5OH$ providing an 82% yield of 3; (c) is 2'deoxy-3',5'-dibenzoyloxy-5-iodouridine, Pd $(PPh_3)_4$, CuI, TEA, DMF giving a 79% yield; (d) $NH_3/CH_3OH$, 90% yield; (e) DMT-Cl, $C_6H_5N$, 81% yield 3'R=H and 5'R=DMT, and (f) ClP $(iPr_2N)(OCH_2CH_2CN)$, $CH_3CN$, 90% yield where HOBt is 1-hydroxybenzotriazole; DIPEA is N,N-diisopropylethylamine; DMF is N,N-dimethylformamide; TEA is triethylamine; and DMT is dimethoxytrityl.

FIG. 3. DNA melting curve for ruthenium modified oligonucleotides.

FIGS. 4A–4C. Synthesis of DMT-FPAU.

DETAILED DESCRIPTION OF THE INVENTION

Figure 1A:
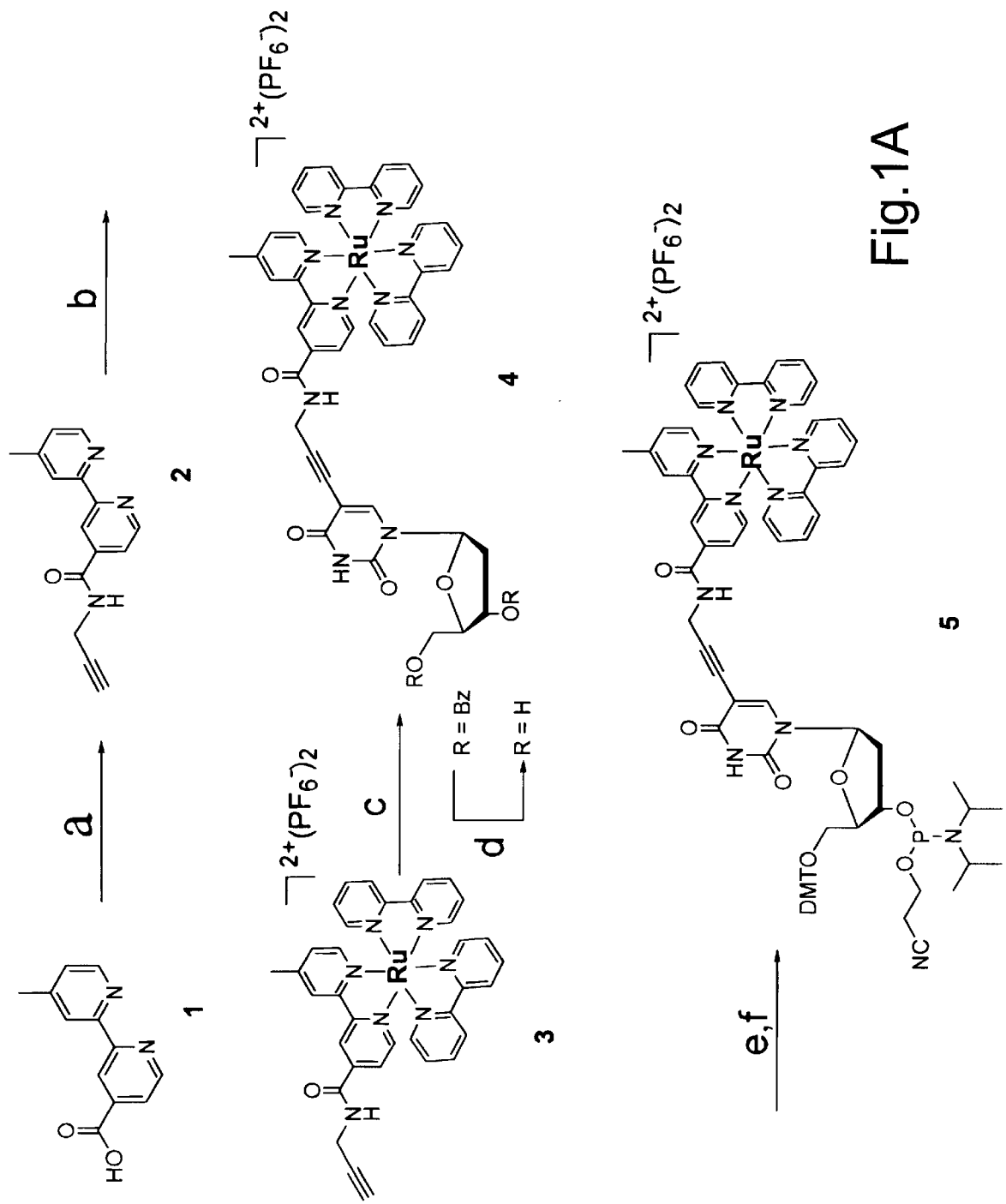

A number of requirements, both synthetic and photophysical, must be met to ensure successful incorporation of a functional photoactive and/or electroactive metal complex into an oligonucleotide. Synthesis of a metallo-oligonucleotide using a metallo-nucleoside phosphoramidite approach, for example, requires: 1) straightforward reactions and purification steps to the precursor metal complex and metallo-nucleoside phosphoramidite, 2) sufficient solubility of the metallo-nucleoside phosphoramidite in acetonitrile for the solid-phase reactions, 3) high stability of the metal complex during oligonucleotide synthesis and deprotection reactions to prevent undesired side reactions and decomposition, and finally 4) efficient coupling of the metallo-nucleoside phosphoramidite using standard automated synthesis. M. J. Gait, *Oligonucleotide Synthesis: A Practical Approach*, IRL Press, Washington, D.C. 1984. Favorable physical properties of the metal complex include: 1) spectroscopically distinguishable metal redox states, 2) tunable electronic structures, 3) energetic excited states, 4) long lifetimes, 5) near unity quantum yield, and 6) photochemical stability.

With these issues in mind, a ruthenium-nucleoside phosphoramidite, 5 (FIGS. 1A–1B) was synthesized. Trisdiimine metal complexes have been found to possess a number of favorable properties including high thermal and photochemical stability, inertness to ligand exchange reactions, tunable electronic structures, long lifetimes in fluid solution ($\tau \approx 1\ \mu s$), and high quantum yields, V. Balzani, A. Juris, M. Venturi, S. Campagne, S. Serroni, *Chem. Rev.* 96 (1996) 759–833; N. H. Damrauer, G. Cerullo, A. Yeh, T. R. Boussie, C. V. Shank, J. M. McCusker, *Science* 275 (1997) 54–57. Metal chromophores of this class are currently used to study a number of photophysical processes including electron-transfer reactions in supramolecular assemblies (A. Juris, V. Balzani, F. Barigelletti, S. Campagna, P. Belser, A. von Zelewsky, *Coord. Chem. Rev.* 84 (1988) 85–277; V. Balzani, S. Campagna. G. Denti. A. Juris, S. Serroni, M. Venturi. *Acc. Chem. Res.* 31 (1998) 26–34; V. Balzani, F. Barigelletti. L. Decola. *T Curr. Chem.* 158 (1990) 31–71; M. Gratzel, K. Kalyanasundaram, *Current. Sci.* 66 (1994) 706–714) and biological systems (H. B. Gray, J. R. Winkler, *Ann. Rev. Biochem.* 65 (1996) 537–561; J. R. Winkler, H. B. Gray, *Chem. Rev.* 92 (1992) 369–379; G. McLendon, *Acc. Chen. Res.* 21 (1988) 160–167). $Ru(bpy_3)^{2+}$ has been selected as an exemplification of the present invention, rather than a phenanthroline analogue, since these complexes, in general, are more potent oxidants in their excited state. Phenanthroline analogues are expected however to be useful as well. The formation of an amide bond with the 4'-carboxylic acid of bipyridine and propargylamine favors localization of the excited state electron on that particular bipyridine, and has been previously shown to enhance the electronic coupling between adjacent $M(bpy_3)^{2+}$ (where M=Ru or Os) in a covalently crosslinked metallo-bipyridine polymeric system. L. M. Dupray, M. Devenney, D. R. Striplin, T. J. Meyer, *J. Am. Chem. Soc.* 119 (1997) 10243–10244. An alkynyl group was introduced on the bipyridine to efficiently cross-couple the metal complex to a halonucleoside using a Pd(0) Heck catalyst. R. F. Heck, *Acc. Chem. Res.* (1978) 146–151; A. Meijere, F.E. Meyer, *Angew. Chem. Int. Ed. Engl.* 33 (1994) 2379–2411. To ensure sufficient solubility in organic solvents and to aid in purification and recrystallization steps a large counter ion such a $PF_6^-$, was used. Other large counter ions can be used, such as $BF_4^-$ and $ClO_4^-$. One skilled in the art will recognize the large number of large positive counter ions which may also be used.

Figure 4A:
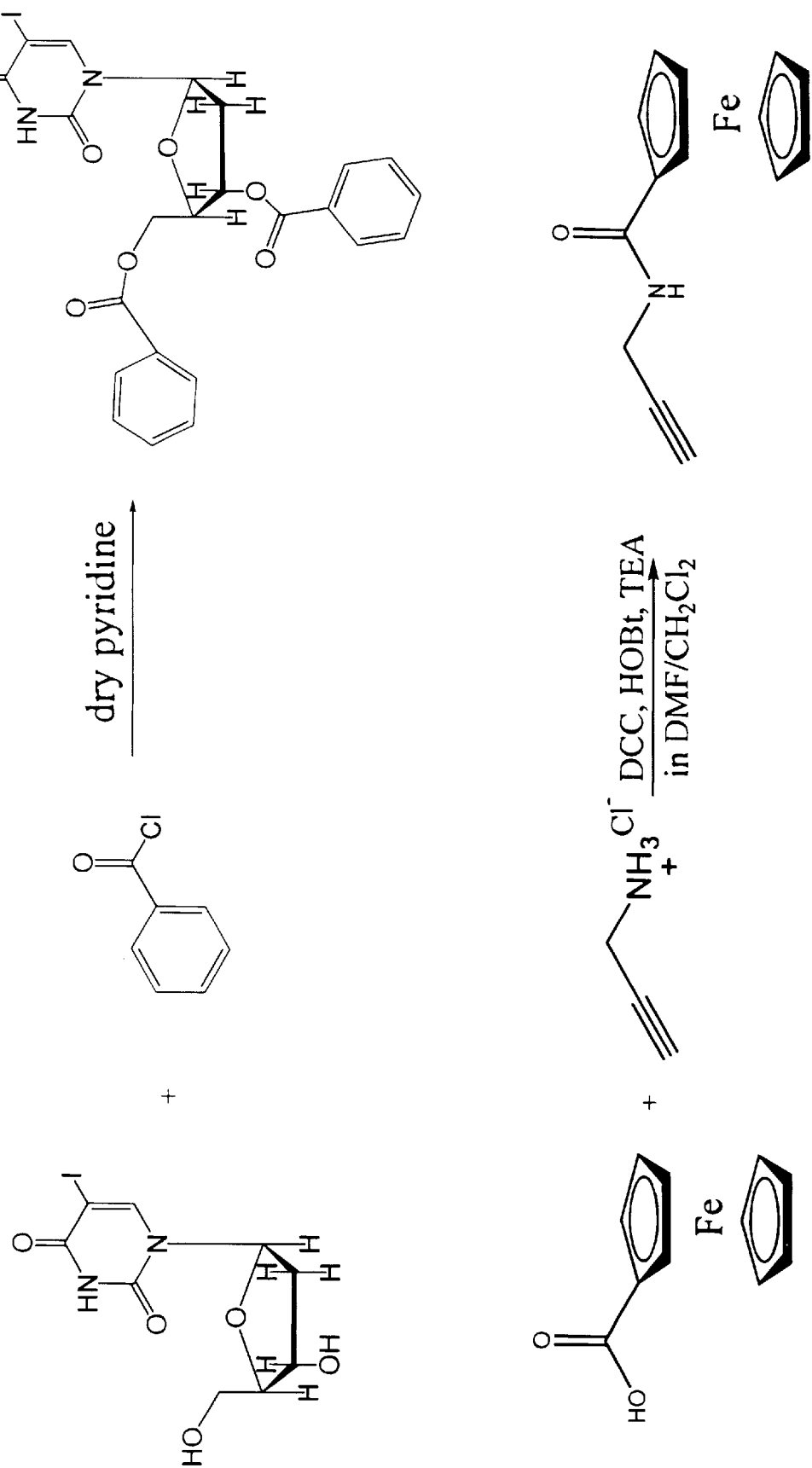
Figure 4B:
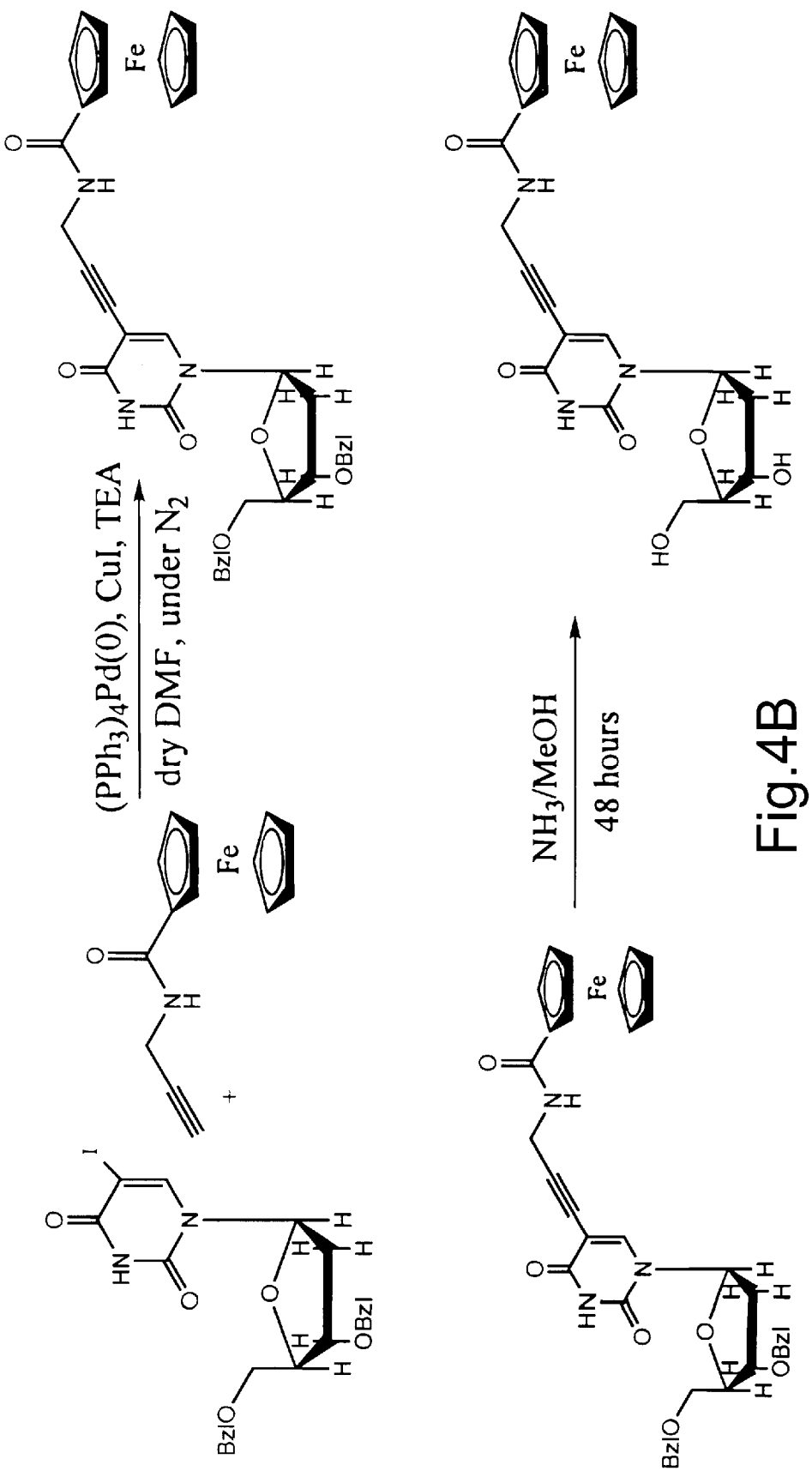
Figure 5A:
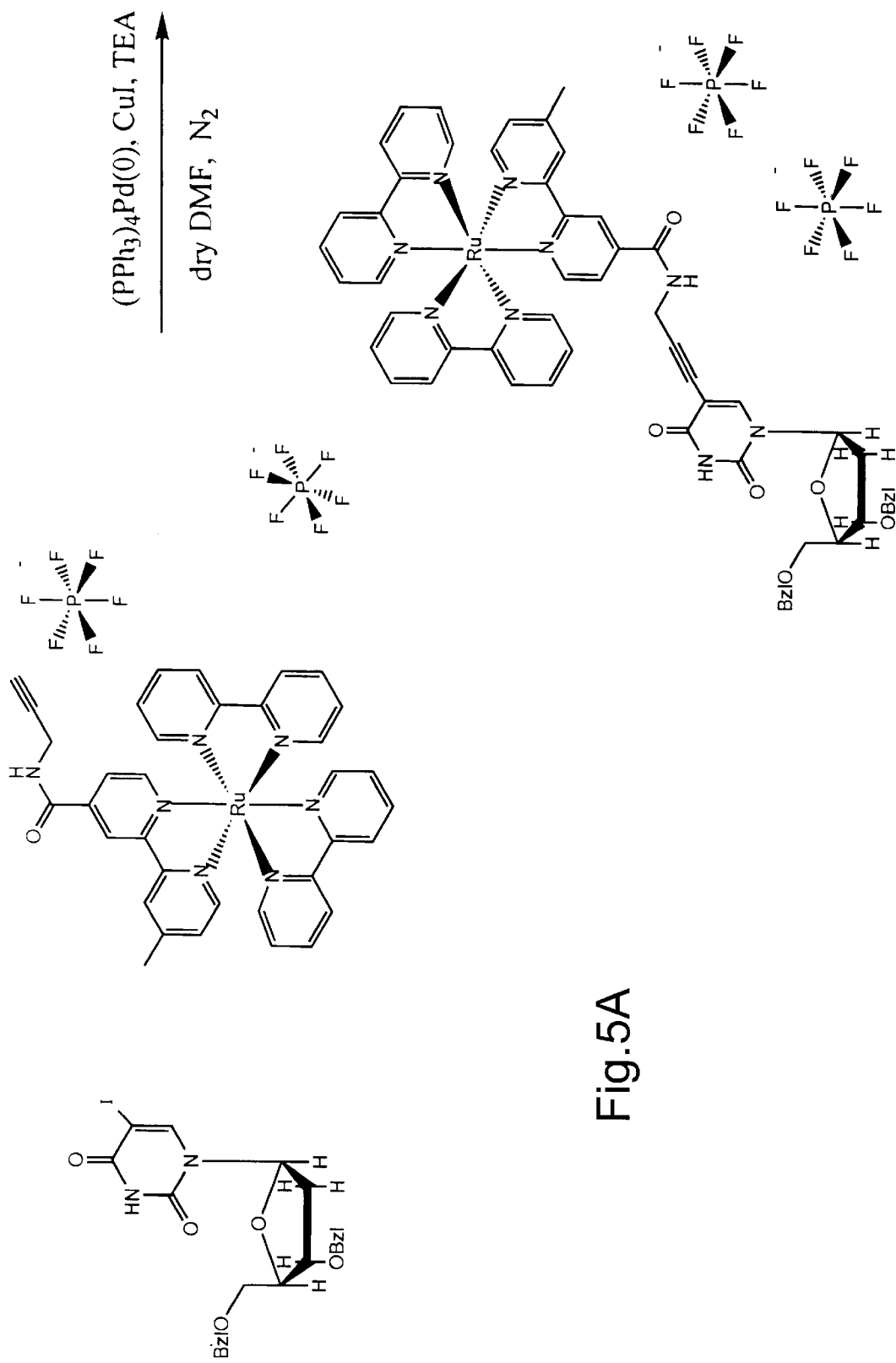
FIGS. 5A–5C. Synthesis of an osmium derivative of the present invention.
Figure 5B:
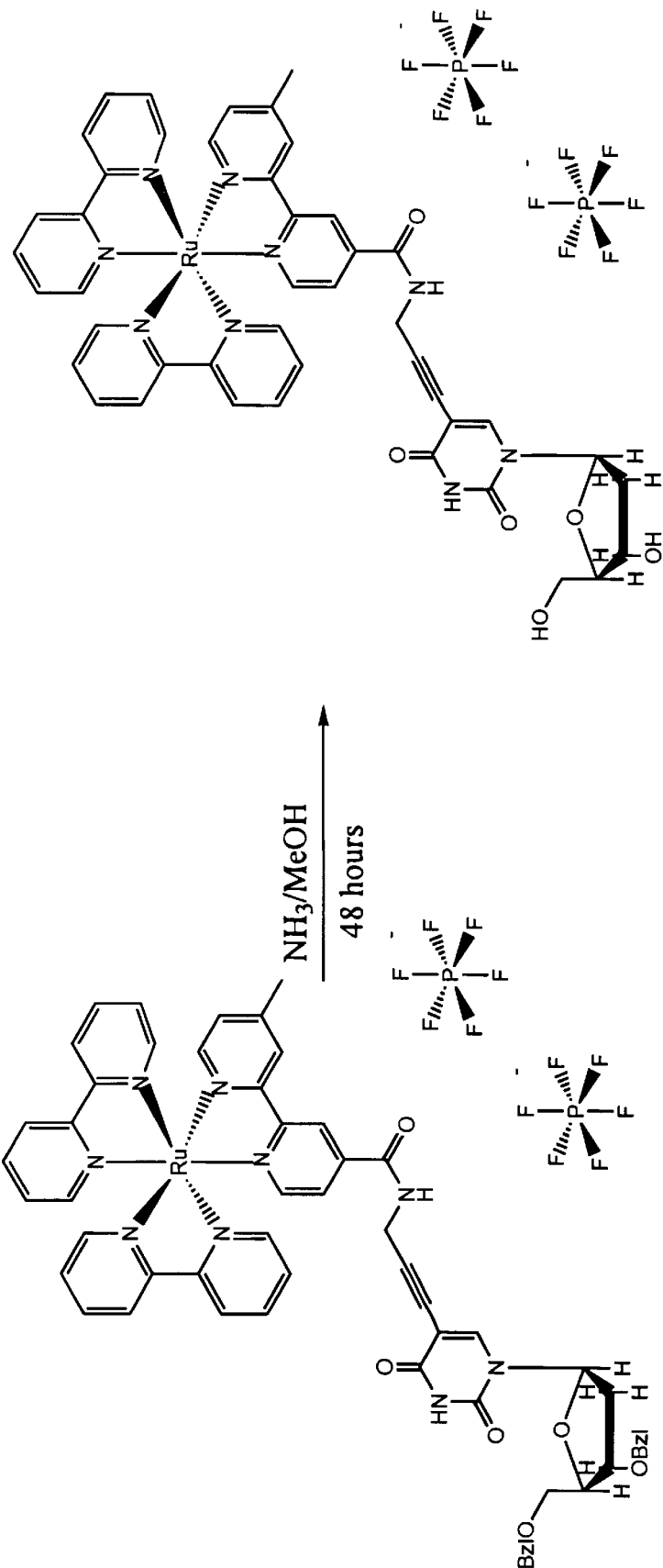
Figure 5C:
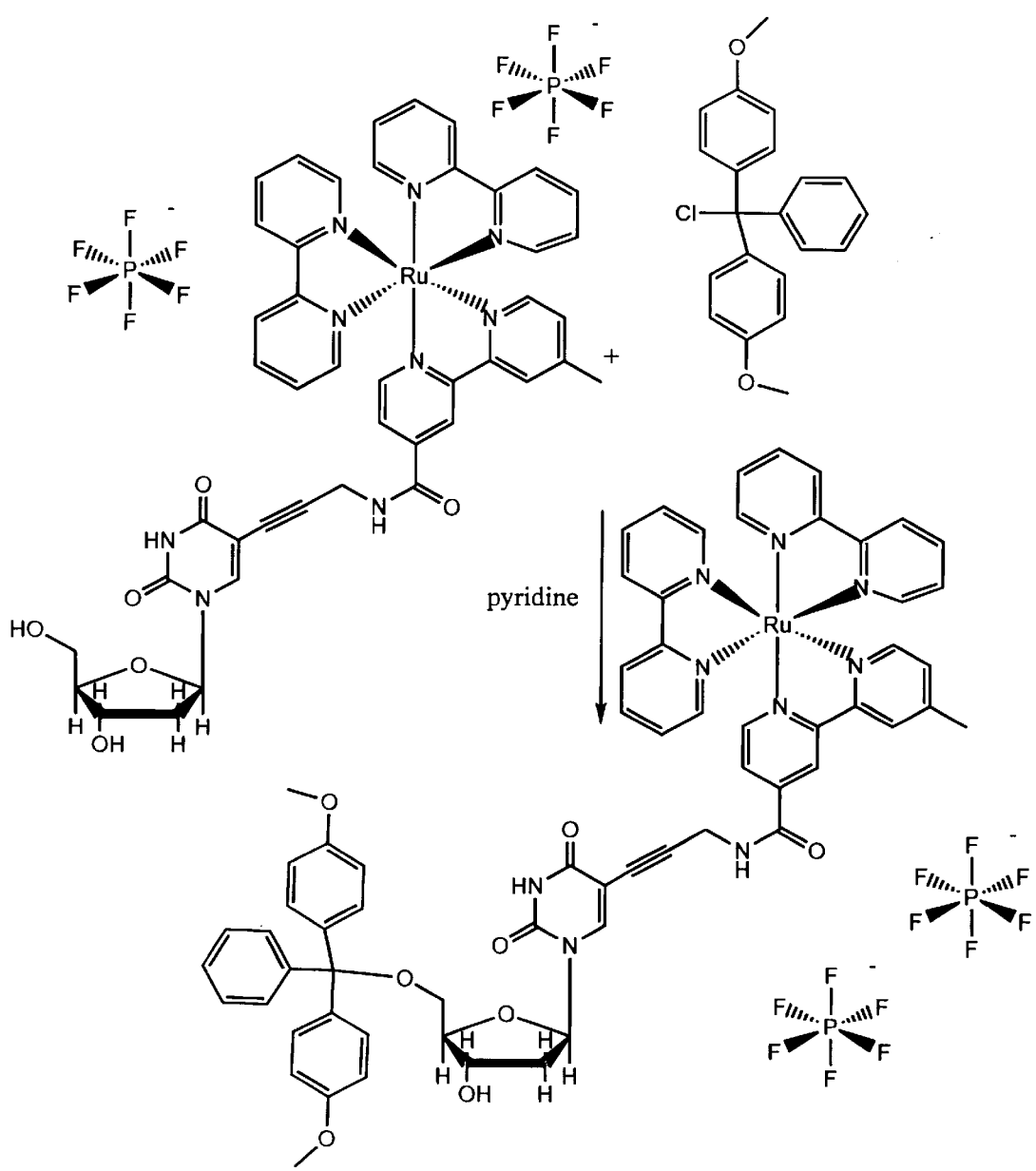
Figure 5D:
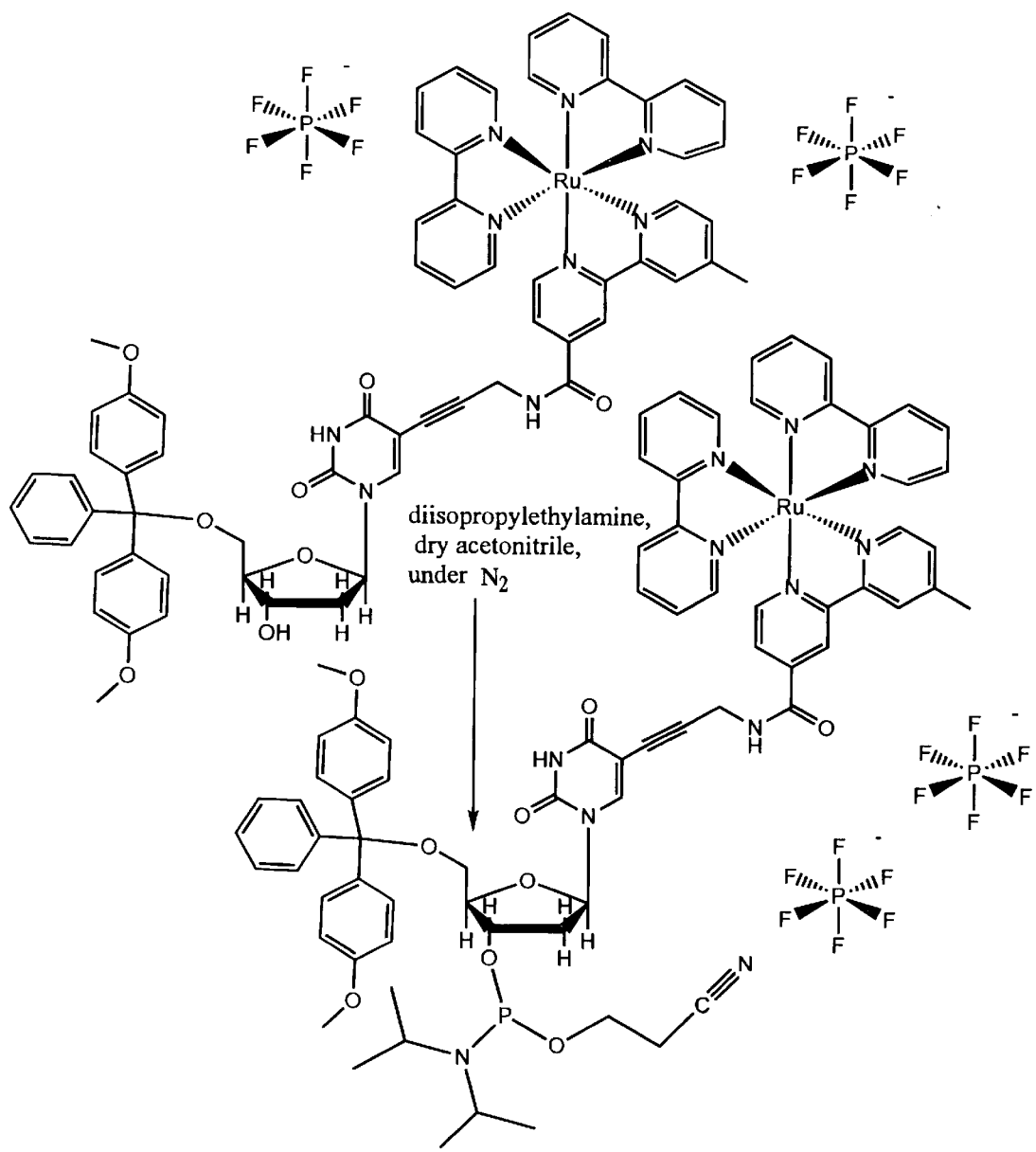
Figure 6A:
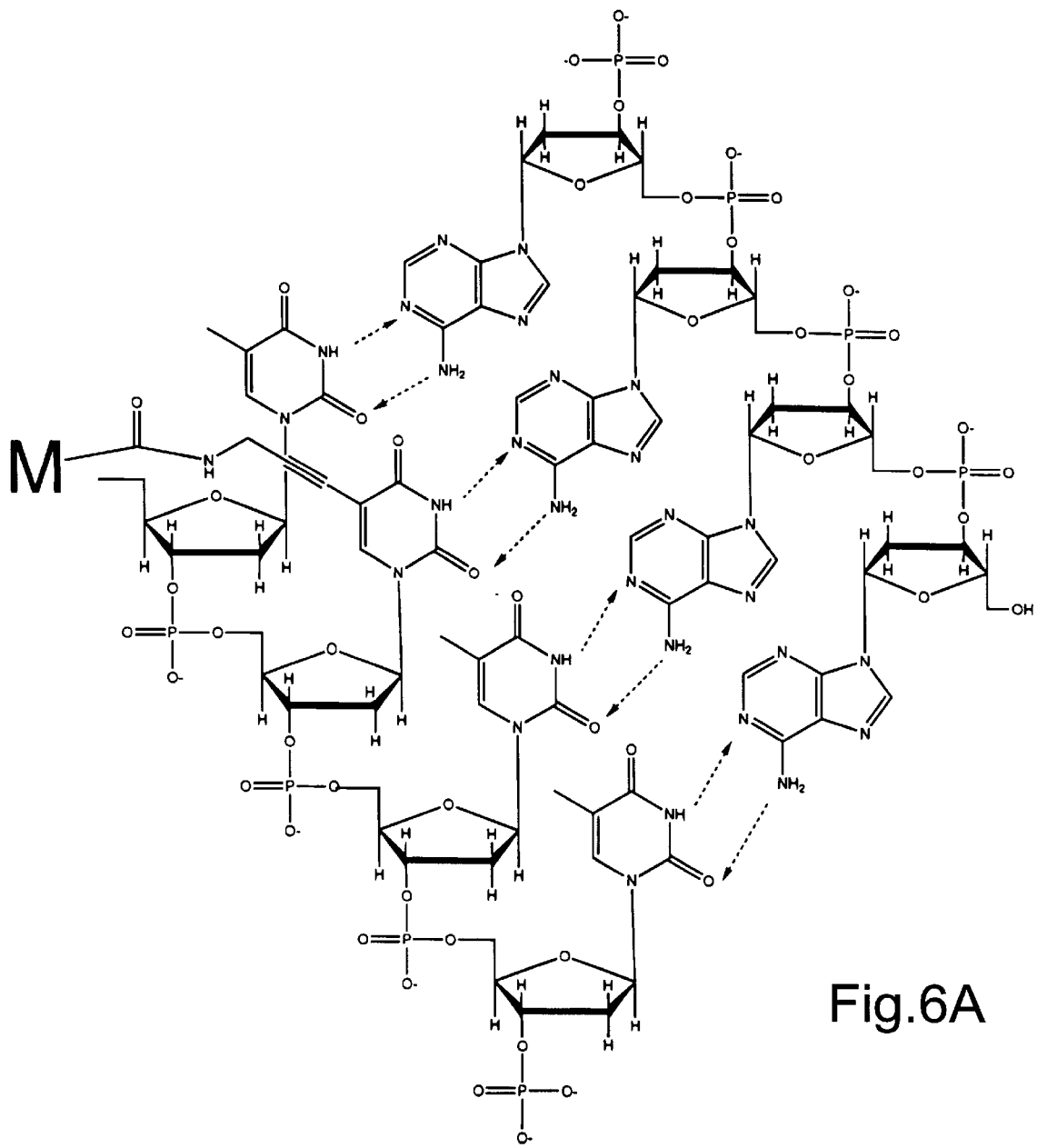
FIGS. 6A–6C. Schematics of metallo-nucleic acid incorporated into a double stranded DNA wherein x represents known types of linkages found in nucleic acids and nucleic acid derivatives.
Figure 6B:
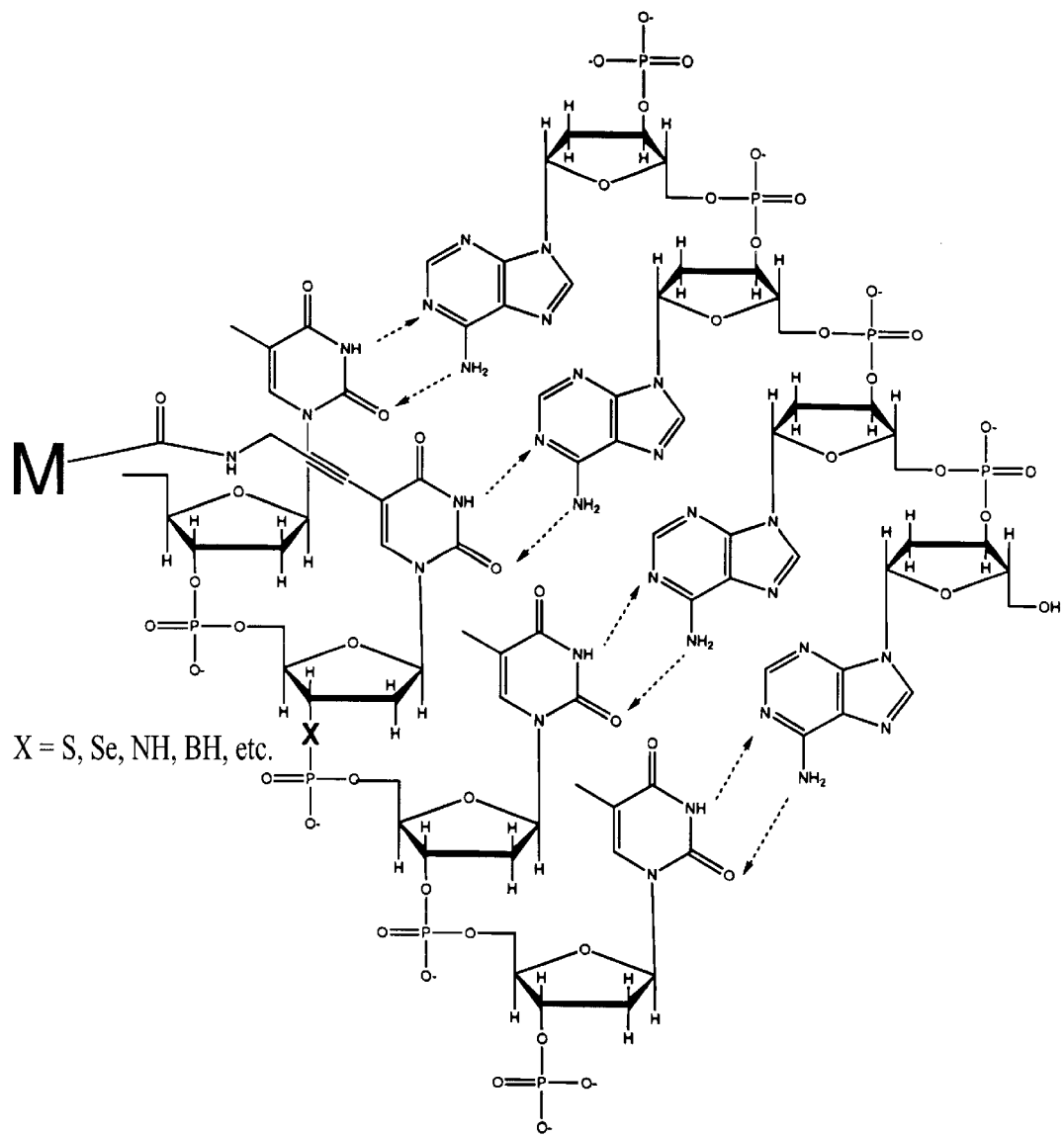
Figure 6C:
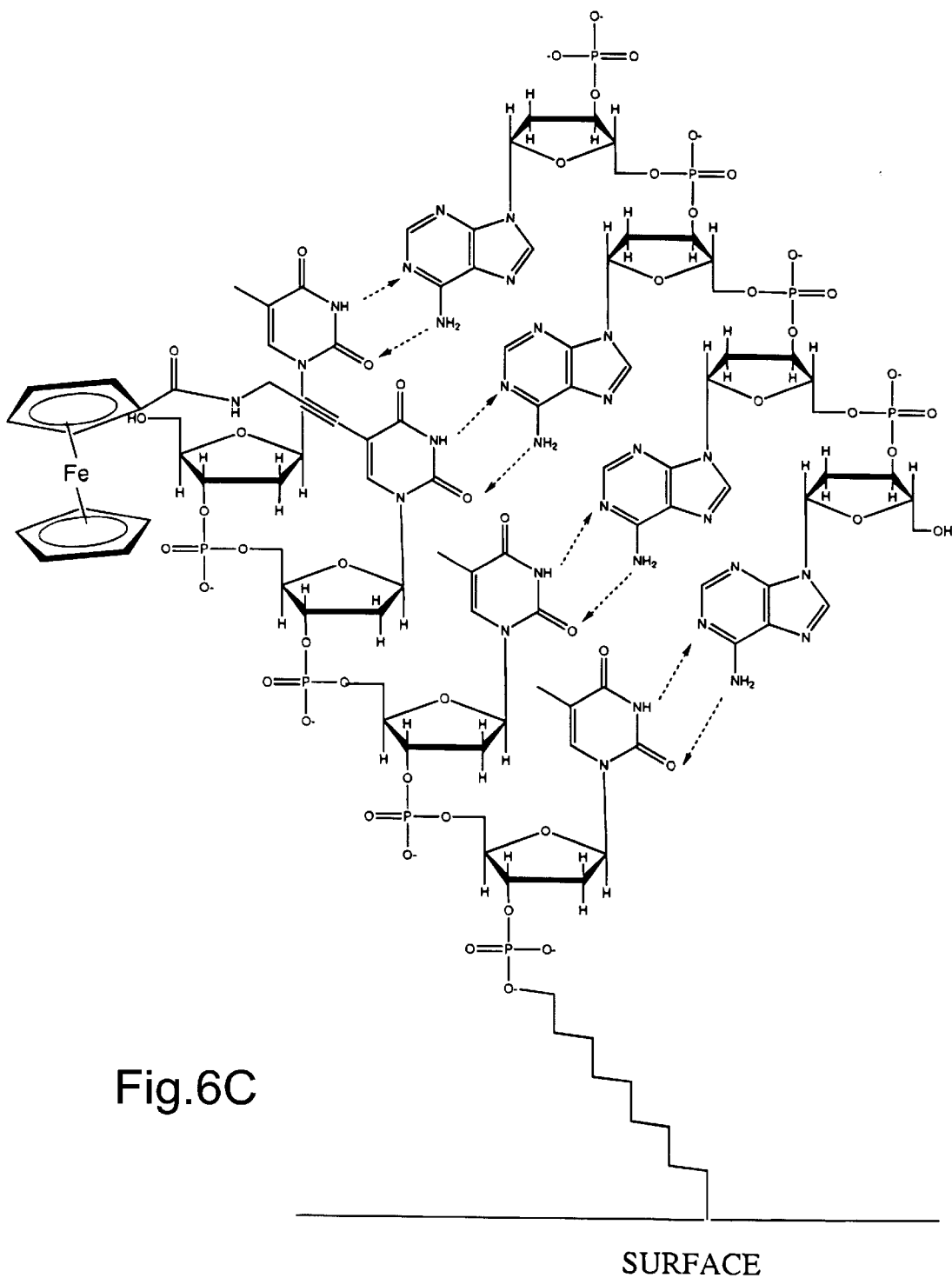

As exemplified in FIGS. 1A–1B, 4'methyl-2-2'-bipyridine-4-carboxylic acid, 1, was coupled to propargyl amine in DMF using dicyclohexylcarbodiimide (DCC). The resulting modified bipyridine, 2, was reacted with $Ru(bpy)_2Cl_2$ to form the tris-bypyridine complex, 3. A $Pd(PPh_3)_4$ cross-coupling reaction between the Ru complex, 3, and 2'-deoxy-3',5'-dibenzoyloxy-5-iodouridine afforded the metallo-nucleoside, 4. Benzoyl deprotection in methanolic ammonia, followed by reaction with 4,4'-dimethoxytrityl chloride and 2-cyanoethylchloro-N,N-diisopropylphosphoramidite yielded the ruthenium-nucleoside phosphoramidite, 5, ready for automated solid-phase synthesis.

In an analogous manner, the hydroxyl group of the phenothiazine derivative, 6, was treated with 2-cyanoethylchloro-N,N'-diisopropylphosphoramidite in the presence of diisopropylethylamine, to yield the phenothiazine phosphoramidite, 7.

An HPLC trace of the ruthenium-modified 2-deoxyuridine, 5, showed one peak, and its elution time was greater than that of 2-deoxyuridine. The MH$^+$-PF$_6^-$ (1036) and $-2$PF$_6^-$ (891) peaks were observed in the FAB-MS, confirming formation of the product.

Figure 2:
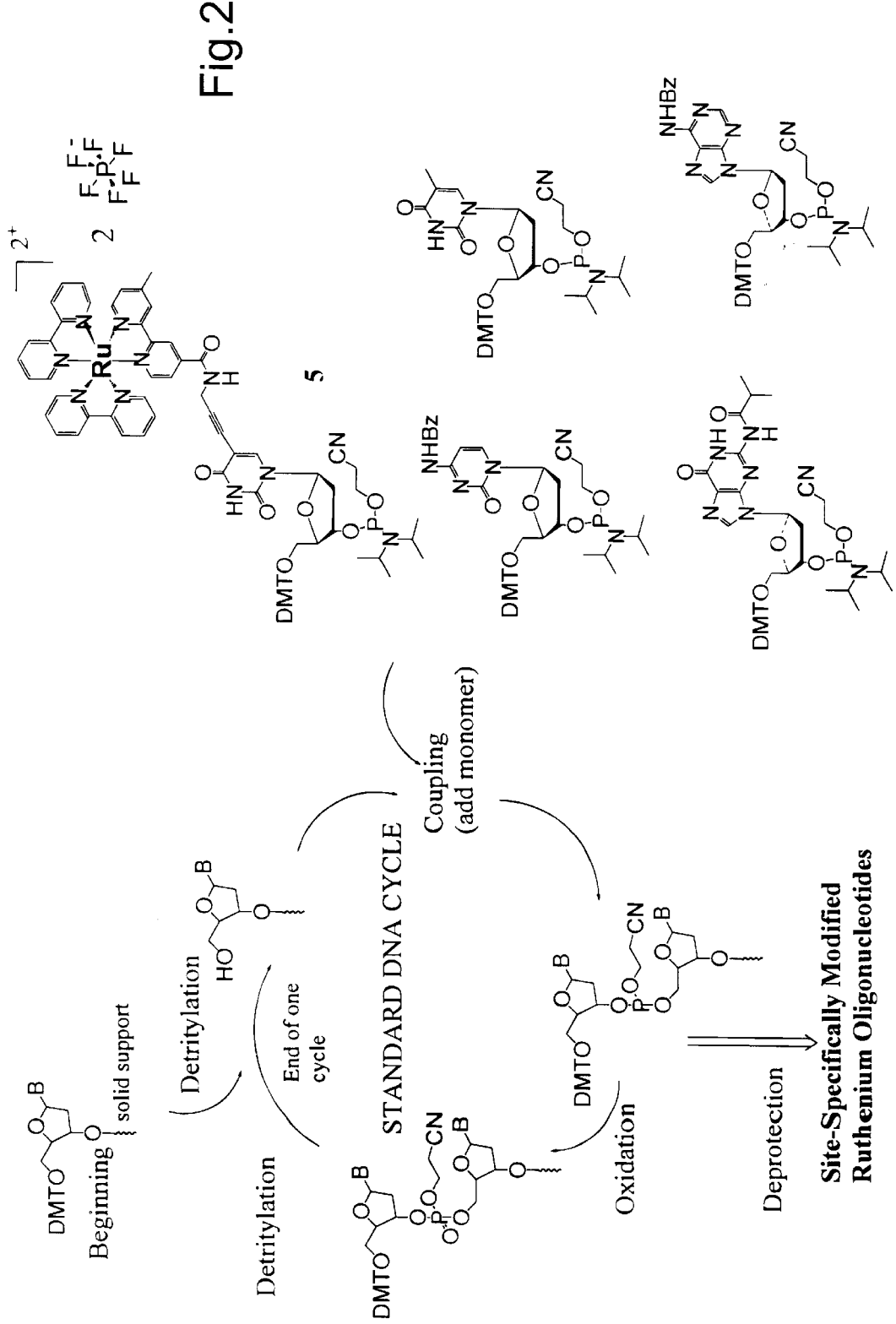
FIG. 2. Automated oligonucleotide synthesis with phosphoramidite derivative of ruthenium nucleoside of the present invention.

The site-specific incorporation of the ruthenium-nucleoside in a 16-mer oligonucleotide was performed using an automated ABI 392 DNA/RNA synthesizer (FIG. 2). All syntheses were accomplished at both the 0.2 and 1 $\mu$mol scales (Table 1).

Table 1

Oligonucleotides Synthesized 6 (SEQ ID NO:1) 5'-TCA ACA GU*T TGT AGC A-3'
7 (SEQ ID NO:2) 5'-U*CA ACA GTT TGT AGC A-3'
8 (SEQ ID NO:3) 5'-TCA ACA GTT TGU* AGC A-3'
9 (SEQ ID NO:4) 5'-TCA ACA GTT TGT AGC A-3'
10 (SEQ ID NO:5) 5'-TGC TAC AAA CTG TTG A-3'
11 (SEQ ID NO:6) 5'-TCG TAC AAA CTG TTG A-NH$_2$-3'

*=ruthenium-modified uridine.

Using the standard coupling protocol, the metallo-nucleobase phosphoramidite was incorporated at different positions within an oligonucleotide. The coupling efficiencies were high (>95%) for all standard bases except for the ruthenium modified analogue which had a coupling efficiency of 40% as determined by measuring the release of DMT during synthesis (498 nm). Others have also observed less than 98% coupling efficiencies when using phosphoramidites that were stencally crowded, of large molecular weight, or of nonstandard nucleobases (M. Grotli et al. Tetrahedron 53, (1997), 11317–11346). Optimization of the automated solid-phase synthesis by varying, for example, the capping times, coupling times, phosphoramidite concentrations, tetrazole concentration, and waiting times are expected to increase coupling efficiencies. Once the ruthenium-modified oligonucleotide was synthesized, the 5'DMT was left on the oligonucleotide for purification ease. The nitrogenous bases and phosphate groups were subsequently deprotected in 30% ammonium hydroxide at 55° C. for 12 hours. Finally, the ruthenium-labeled oligonucleotide was purified using a standard Poly-PakTM cartridge (Glen Research) and reverse-phase HPLC methods (C18; 0.1 M TEAA/CH$_3$CN; 10–50% gradient over 50 minutes; monitoring at 254 and/or 450 nm). The ruthenium-modified oligonucleotides exhibit one peak in an HPLC trace, with retention times greater than the corresponding unmodified oligonucleotide. MALDI, Matrix Assisted Laser Desorption Ionization-time of flight, mass spectrometry of the metallo-oligonucleotide also confirms formation [e.g., ruthenium modified oligonucleotide 8, MALDI (5058.25; 5055.6; calculated: found +3)].

Thermal denaturation experiments on the unmodified and modified oligonucleotide duplexes showed a moderate decrease in thermal stability when the ruthenium was introduced into the middle of the oligonucleotide sequence compared to an unmodified duplex (150 mM sodium phosphate; pH 7; monitoring at 260 nm). (FIG. 3) The melting temperature (Tm) of the unmodified duplex, duplex. 9•10 (see Table 1), was 60° C., compared to 51° C. for the ruthenium-labeled duplex, duplex 6•10. This effect was diminished when the metal complex was on the terminal nucleotide of the oligonucleotide sequence (duplex 7•10), Tm=60). This decrease in Tm with the ruthenium-modified oligonucleotide duplex, 6•10, was of lesser magnitude than that observed for a single mismatch in a duplex. These data illustrate that the metallo-oligonucleotides form stable duplexes at room temperature, and are amenable to photo-physical characterization and further study.

The ruthenium-uridine described herein is a suitable chromophore for reductive quenching studies since it is photochemically stable, inert to ligand substitution reactions, possesses an energetic excited state (0.84 eV), and a long lifetime in fluid solution. Moreover, the excited-state electron is localized on the bipyridine attached to the uridine. The electron-transfer quencher, phenothiazine is known to be a very efficient electron donor for quenching *Ru(bpy)$_3^{2+}$ .(Mecklenburg, S. L.; Peek, B. M.; Schoonover, J. R.; McCafferty, D. G.; Wall, C. G.; Erickson, B. W.; Meyer, T. J. J. Am. Chem. Soc. 1993, 115, 5479–5495. Slate, C. A.; Striplin, D. R.; Moss, J. A.; Chen, P.; Erickson, B. W.; Meyer, T. J. J. Am. Chem. Soc. 1998, 120, 4885–4886.) The biomolecular electron-transfer reaction between compounds 4 and 7 of FIGS. 1A–1B was studied in solution by varying the quencher concentration. Stem-Volmer analysis yielded a quenching rate constant (kq) of $1.3\times10^9$ M$^{-1}$ s$^{-1}$. Based on the reduction potential of PTZ+/0 (0.76 eV), the driving force for this electron-transfer reaction was estimated to be approximately 0.1 eV.

In this DNA-mediated electron-transfer system, the electron donor and acceptor were covalently attached to different oligonucleotide strands and separated by about 30 Å. First, the complimentary duplex containing only the ruthenium acceptor (5'-TCA ACA GU*T TGT AGC A-3' (SEQ ID NO:1); 5'-TGC TAC AAA CTG TTG A-3' (SEQ ID NO:5)) was synthesized (U*=Ru(diimine)$_3^{2+}$ linked uridine). The emission maximum for this ruthenium-labeled oligonucleotide duplex was centered at 660 nm and the emission lifetime was measured to be 540 ns at 20° C. in phosphate buffer (monitoring at 640 nm after 455 nm pulse excitation). Next, phenothiazine (PTZ) was attached to the 5'-terminal of the complimentary sequence of the ruthenium labeled oligonucleotide (5'-TCA ACA GU*T TGT AGC A-3' (SEQ ID NO:1); 5'-PTZ-TGC TAC AAA CTG TTG A-3' (SEQ ID NO:5)). Reductive quenching of the excited state was observed, and the rate constant was determined to be 2.6× $10^5$ s$^{-1}$. The lifetime and electron-transfer rates were measured using a Laser Photonics LN1000 Nitrogen Laser-LN102 dye laser (coumarin 460 dye). The emission was monitored at right angle with a Macpherson 272 monochromator and Hammamatsu R666-10 PMT at 22° C. The signal was processed by a LeCroy 7200A transient digitizer interfaced with an IBM-PC. The excitation wavelength was 455 nm and the monitoring wavelength was 640 nm. Power at the sample was 60 W/pulse.mm3 as measured by a Molectron J3-09 power meter. The measured instrument response function is 10 ns (FWHM). The acquired emission decay curves were analyzed by a locally written software based on the Marquardt algorithm. The data were fit to a single exponential. The residuals between the experimental and fitted curves were less than 2%. The electron-transfer rate constant was determined using the following equation: k=1/t−1/t0. Over the temperature range of 5 to 30° C., the rate constant increased slightly from 2.5 to $2.8\times10^5$ s$^{-1}$.

The synthetic strategy of the present invention will be recognized to be a general one which is amenable to attaching electron donors and acceptors at site-specific locations; and these modified duplexes are suitable for electron-transfer measurements. The microsecond electron-transfer rate was measured over this extended distance indicates that long-range electron transfer from phenothiazine to *Ru(diimine)$_3^{2+}$ occurs. Importantly, the Ru(diimine)$_3^{2+}$ modified nucleoside and phenothiazine phosphoramidites expand the current repertoire of available DNA electron-transfer probes.

In a further embodiment, the present invention provides labeled or detectable moieties which are attached to the 5', 3' or 2' carbon of a nucleoside or nucleotide sugar. As an exemplification of this embodiment, DNA was labeled at the 5'-amino-ribose of an oligonucleotide with a substitutinally inert transition metal complex, by automated solid phase synthesis. Specifically, a Ru(diimine)$_3^{2+}$-thymidine derivative, 5'-[Ru(bpy)$_2$(4-m-4'ca-bpy)$^{2+}$]-thymidine, was synthesized and subsequently incorporated in an oligonucleotide as an active phosphoramidite complex.

Figure 7:
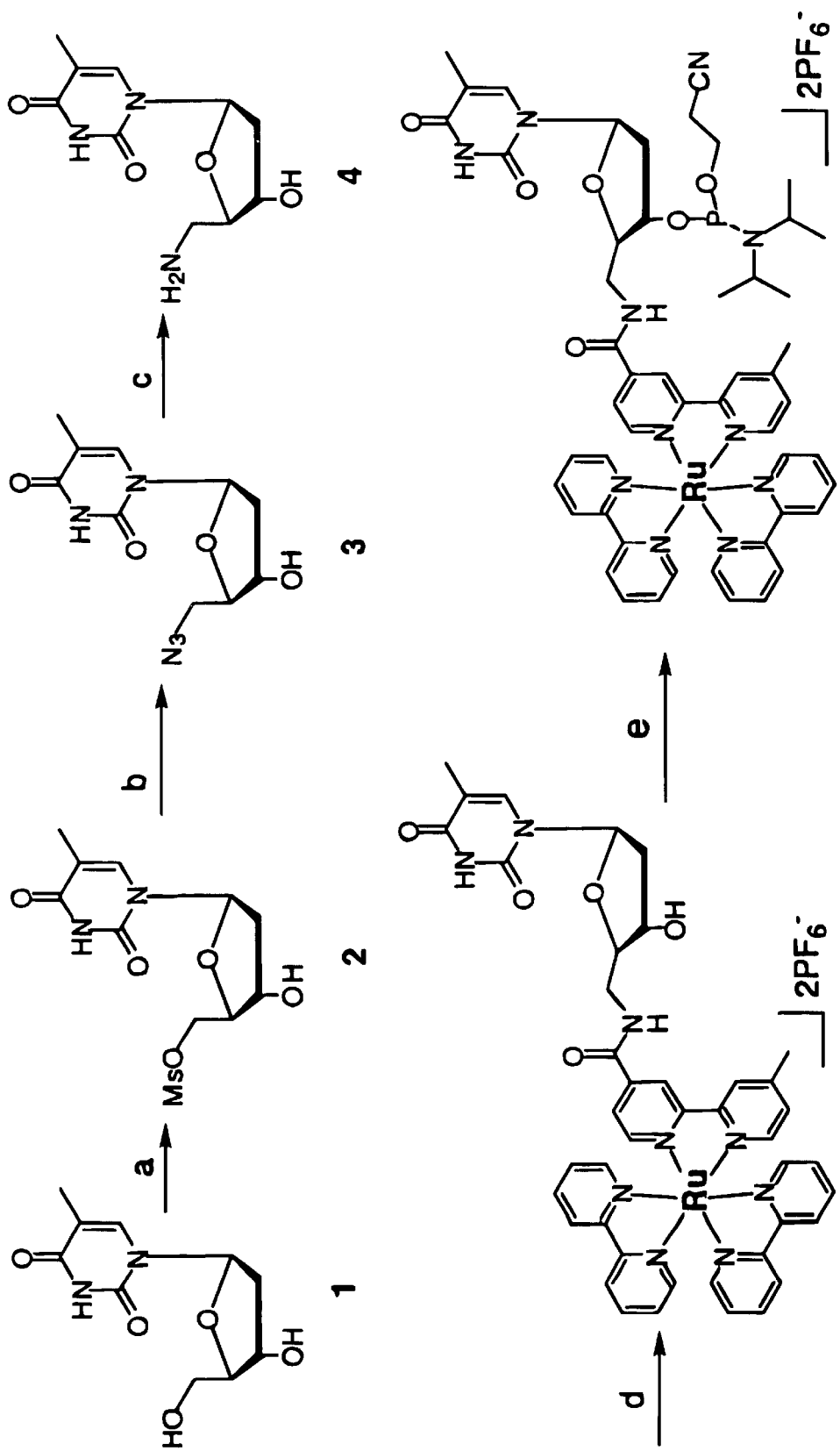
FIG. 7. Synthesis scheme for nucleotide derivative according to the present invention wherein the following conditions apply: a) MsCl/pyridine, 0° C., 12 h, 77% yield; b) $LiN_3$/DMF, 90° C., 3 h, 73% yield; c) $PPh_3$/dioxane, $NH_4OH$, 25° C., 12 h, 72% yield; d) CDI/DMF, LH-20/THF, $Ru(bpy)_2$(4-m-4'-ca-bpy), 25° C., 12 h, 80% yield; e) 2-cyanoethylchloro-N,N-diisopropylphosphoramidite, DIPEA, $CH_3CN$, 25° C., 2 h (yield >95% TLC).
Figure 8:
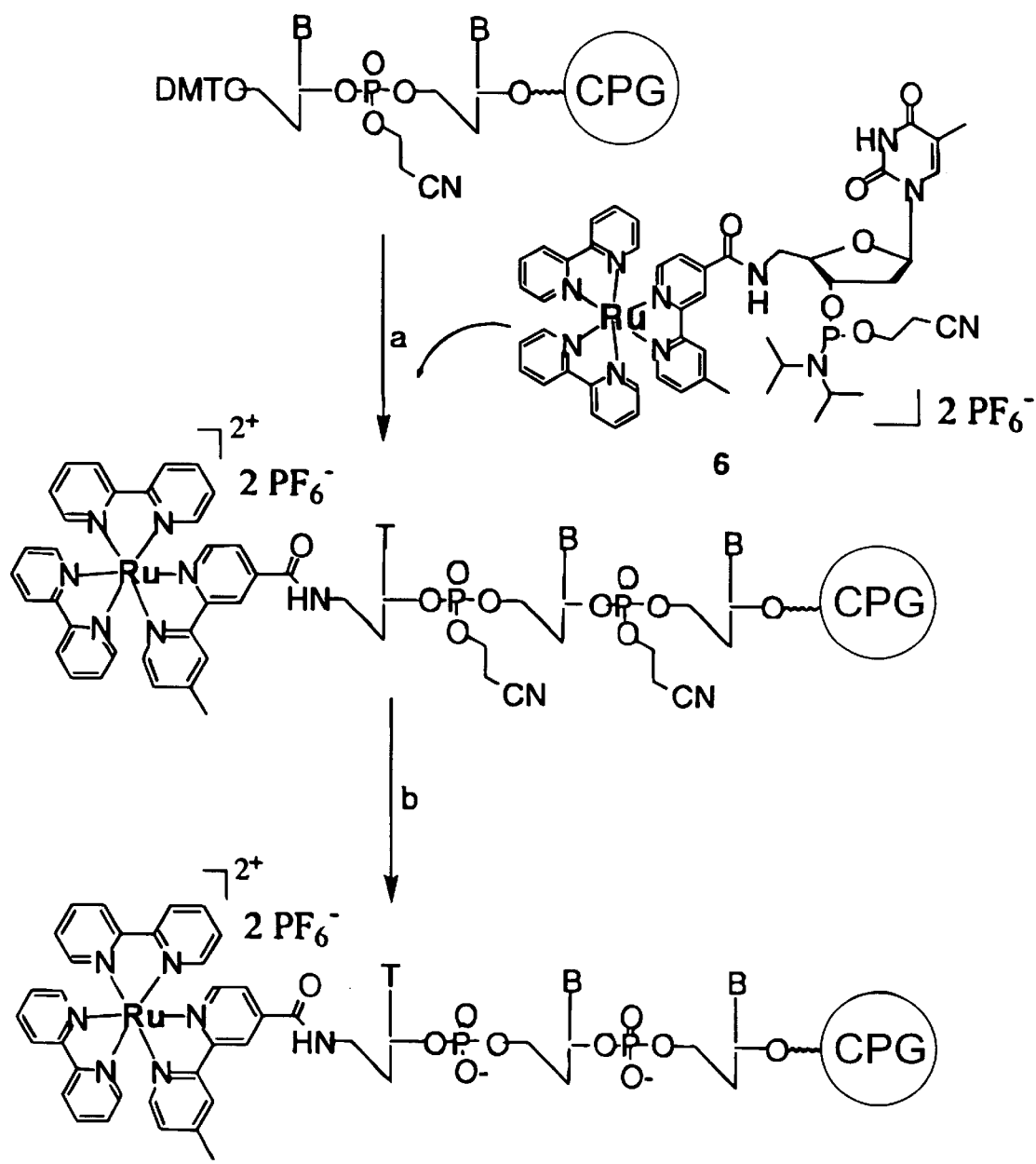
FIG. 8. Exemplification of automated synthesis with a nucleotide derivative of the present invention wherein the following conditions apply: (a) normal synthesis; (b) 30% $NH_3$, 55° C., 16 h. B=nucleotide bases A, C, G or T.

The synthesis of thymidine derivative is described with reference to FIG. 7. The Ru(diimine)$_3^{2+}$ derivatized-phosphoramidite, 6, for automated DNA synthesis was synthesized in five steps starting from thymidine. As shown in FIG. 7, the 5'-position of thymidine was first converted from hydroxyl to an amine. Thymidine was dissolved in pyridine and reacted with methanesulfonyl chloride to form compound 2. Next, the mesyl group was substitute with an azide, and subsequently reduced with PPh$_3$ to yield the 5'-amino-thymidine, 4. The mono-carboxylic acid derivatized Ru(diimine)$_3^{2+}$ complex, Ru(bpy)$_3$(4-m-4'-ca-bpy)$^{2+}$, was then coupled as the activated ester to 5-amino-thymidine, 4, in DMF using CDI. Finally, 5 was reacted with 2-cyanoethyl-chloro-N,N-diisopropylphosphoramidite in dry CH$_3$CN to afford the metallo-phosphoramidite, 6. The ruthenium-thymidinephosphoramidite was used in an oligonucleotide solid-phase synthesizer whereby, in the last coupling tep, the ruthenium-modified thymidine phosphoramidite was introduced, as shown in FIG. 8. All syntheses were performed at the 1.0 μmol scale using the standard coupling protocol except that the final step proceeded for 15 minutes to ensure sufficient time for the Ru(diimine)$_3^{2+}$-thymidine phosphoramidite to react with the 5'-terminal alcohol of the oligonucleotide sequence. Once the ruthenium-labeled oligonucleotide was synthesized, the oligonucleotide was cleaved from the column. Next, the nitrogenous bases and phosphate groups were deprotected in 30% ammonium hydroxide at 55° C. for 16 hours (see Table 2).

Table 2

Oligonucleotides Synthesized 12 (SEQ ID NO:7) 5'-*TTCAACAGTTTGT-3'
13 (SEQ ID NO:8) 5'-*TCAACAGTTTGTAGCA-3'
14 (SEQ ID NO:9) 5'-*TGCTACCCTCTGTTGA-3'
15 (SEQ ID NO:10) 5'-*TTCAACAGTTTGTAGCA-3'
16 (SEQ ID NO:11) 5'-TTCAACAGTTTGT-3'
17 (SEQ ID NO:12) 5'-TGCTACCCTCTGTTGA-3'
18 (SEQ ID NO:13) 5'-TTCAACAGTTTGTAGCA-3'
19 (SEQ ID NO:14) 5'-ACAAACTGTTGAA-3'
20 (SEQ ID NO:15) 5'-TCAACAGAGGGTAGCA-3'
21 (SEQ ID NO:16) 5'-TGCTACAAACTGTTGAA-3'

*=ruthenium-modified thymidine

Figure 9:
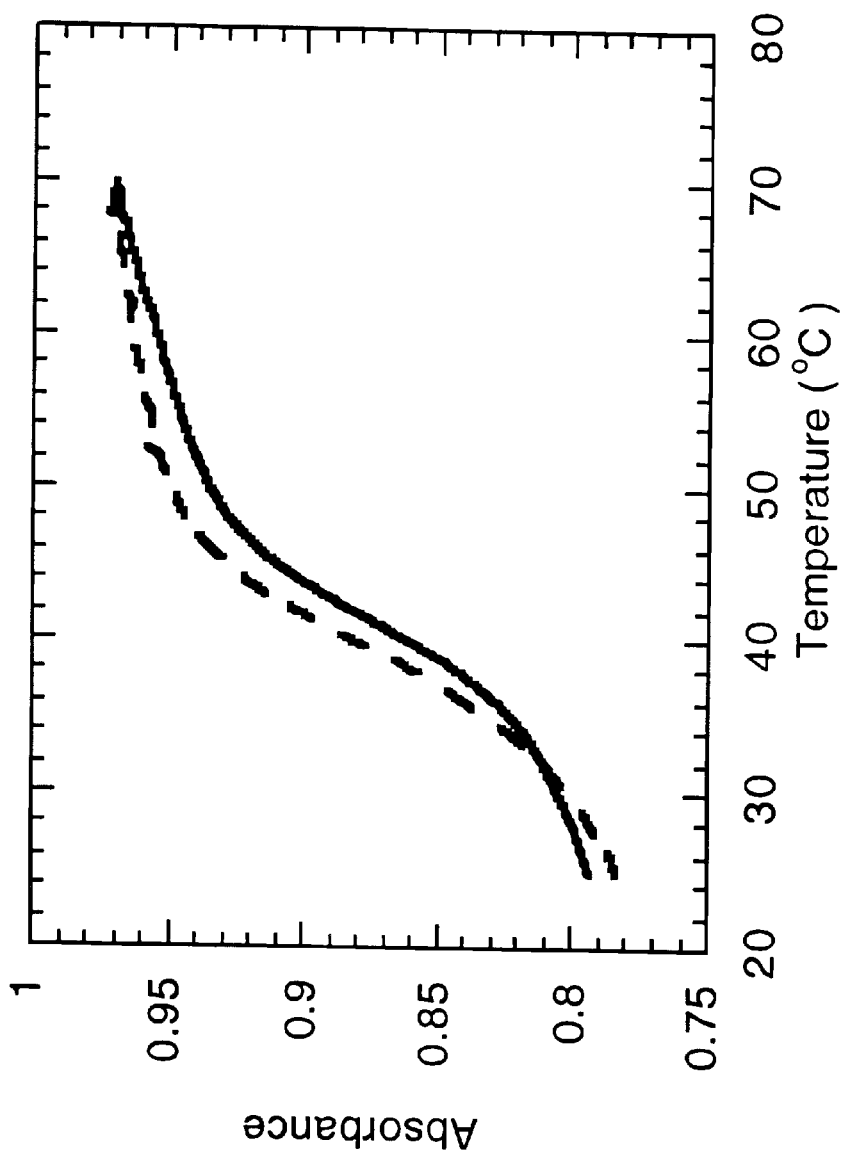
FIG. 9. Thermal denaturation curve of oligonucleotides according to Table 2.
Figure 10:
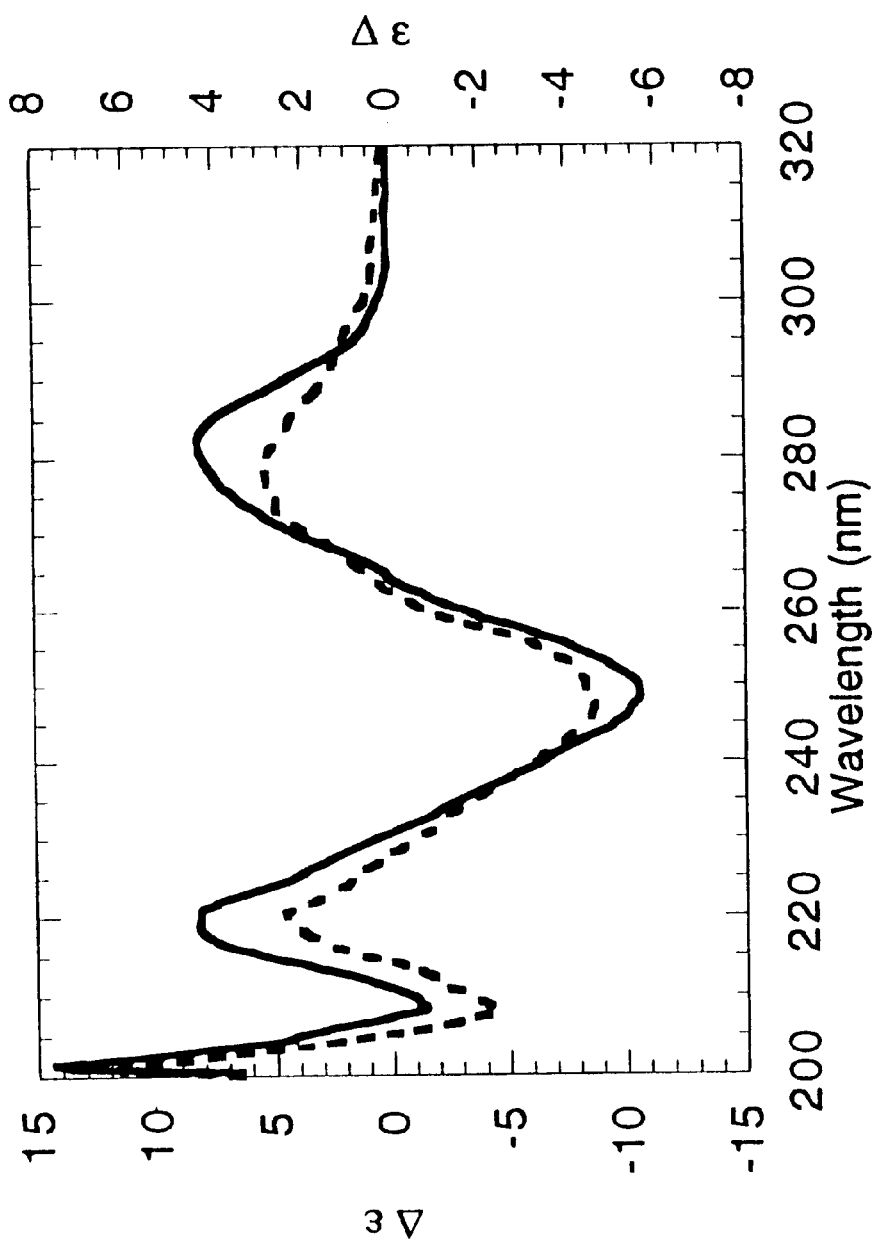
FIG. 10. Spectrum of B– DNA.

As shown in FIG. 9, the thermal denaturation curve for the unlabeled (11•15) and Ru(diimine)$_3^{2+}$ labeled (12•19) 13-mer oligonucleotide duplexes are similar. The decrease in the melting temperature from 42° C. to 39° C., respectively, is small and this magnitude of change is also observed with larger duplexes (e.g., 18•21, 51° C.; 15•21, 52° C.). This relatively small change indicates that labeling the 5'-terminal nucleotide of the oligonucleotide does not dramatically alter the duplex structure of DNA. These results are further supported by circular dichroism (CD) spectroscopy experiments. CD spectra of the unlabeled (16•19) and Ru(diimine)$_3^{2+}$ labeled oligonucleotides (12•19) are similar, and the characteristic spectral features for B-DNA are present (FIG. 10). In comparison to other labeling sites in an oligonucleotide, attaching a Ru(diimine)$_3^{2+}$ to the terminal nucleobase of an oligonucleotide does not alter the melting temperature nor the CD spectrum compared to the unlabeled analog, (16•19). On the other hand, the melting temperature decreases by approximately 15° C. when the Ru(diimine)$_3^{2+}$ label is linked to the 5'-terminal phosphate. The 5'-position of thymidine is a suitable site for introducing labels such as transition metal complexes.

The absorption spectrum of the ruthenium-labeled oligonucleotide single strand exhibits the characteristic metal-to-ligand charge-transfer band ($^1$MLCT-$^1$A$_1$) centered at 450 nm analogous to Ru(bpy$_3$)$^{2+}$ Excitation of the MLCT band of the ruthenium modified single strand oligonucleotide produces an emission centered at 610 nm corresponding to the $^3$MLCT excited state. This emission is essentially unchanged when a duplex is formed. This emissive metallo-oligonucleotide can be attached to a surface and visualized with a confocal microscope (excitation at 488 nm, emission monitored at 600 nm).

Figure 11:
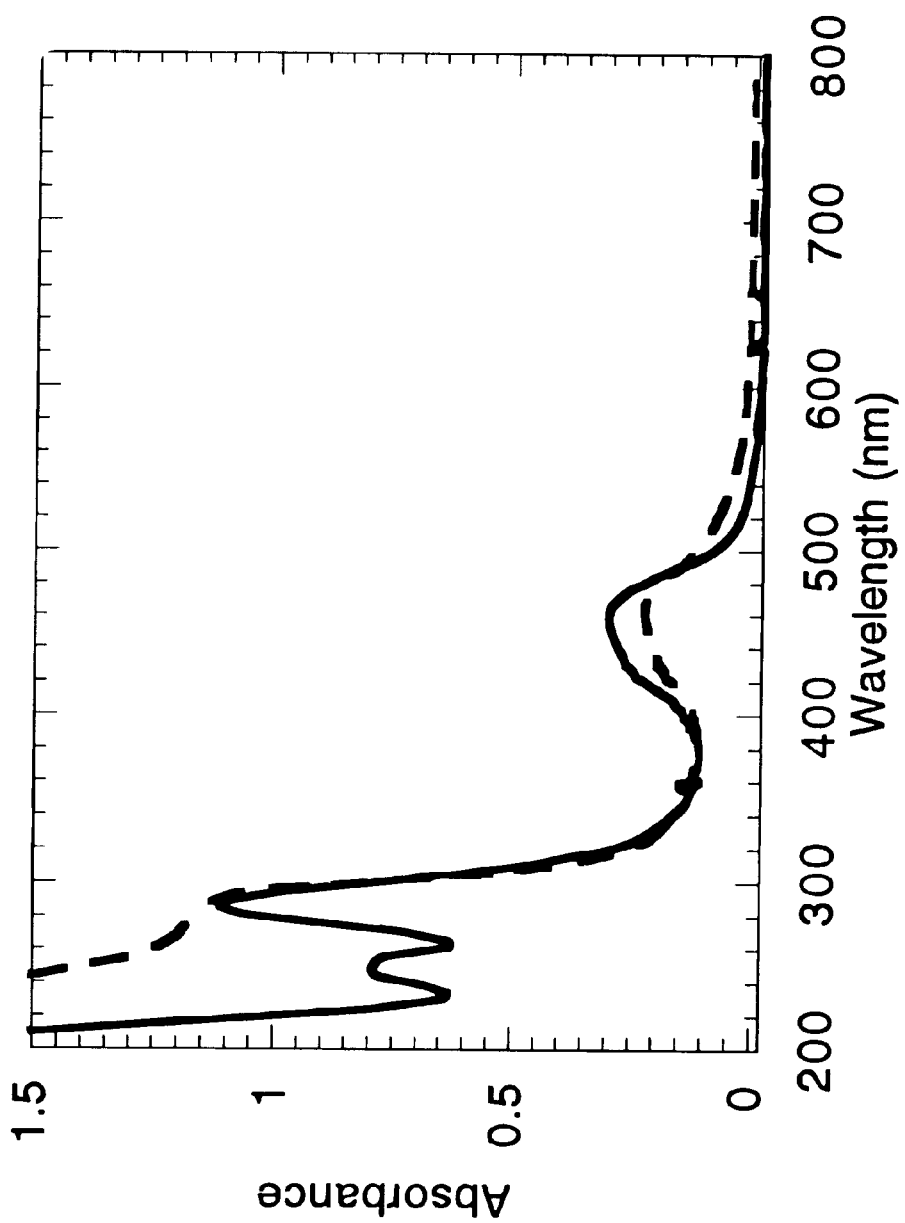
FIG. 11. Absorption spectrum, of $Ru(bpy)_3^{2+}$.

The Ru(diimine)$_3^{2+}$ derivatized thymidine complex, 5 (FIG. 7), exhibits the characteristic metal-to-ligand charge transfer band ($^1$MLCT-$^1$A$_1$), centered at 450 nm in the absorption spectrum, analogous to Ru(bpy)$_3^{2+}$ (FIG. 11). At higher energy the absorbances at 260 and 280 nm are the n-π* and π-π* transitions of thymidine and bipyridine, respectively. Excitation of the MLCT band at 450 nm produces an emission centered at 666 nm in phosphate buffer (see FIG. 12), and slightly red-shifted from Ru(bpy)$_3^{2+}$ (625 nm). The emission lifetime of compound 5 is 430 ns in phosphate buffer (25° C.). These absorption and emission results are also consistent with similar Ru(diimine)$_3^{2+}$ complexes designed for labeling the 5-terminal phosphate or the nucleobase of an oligonucleotide.

Figure 13:
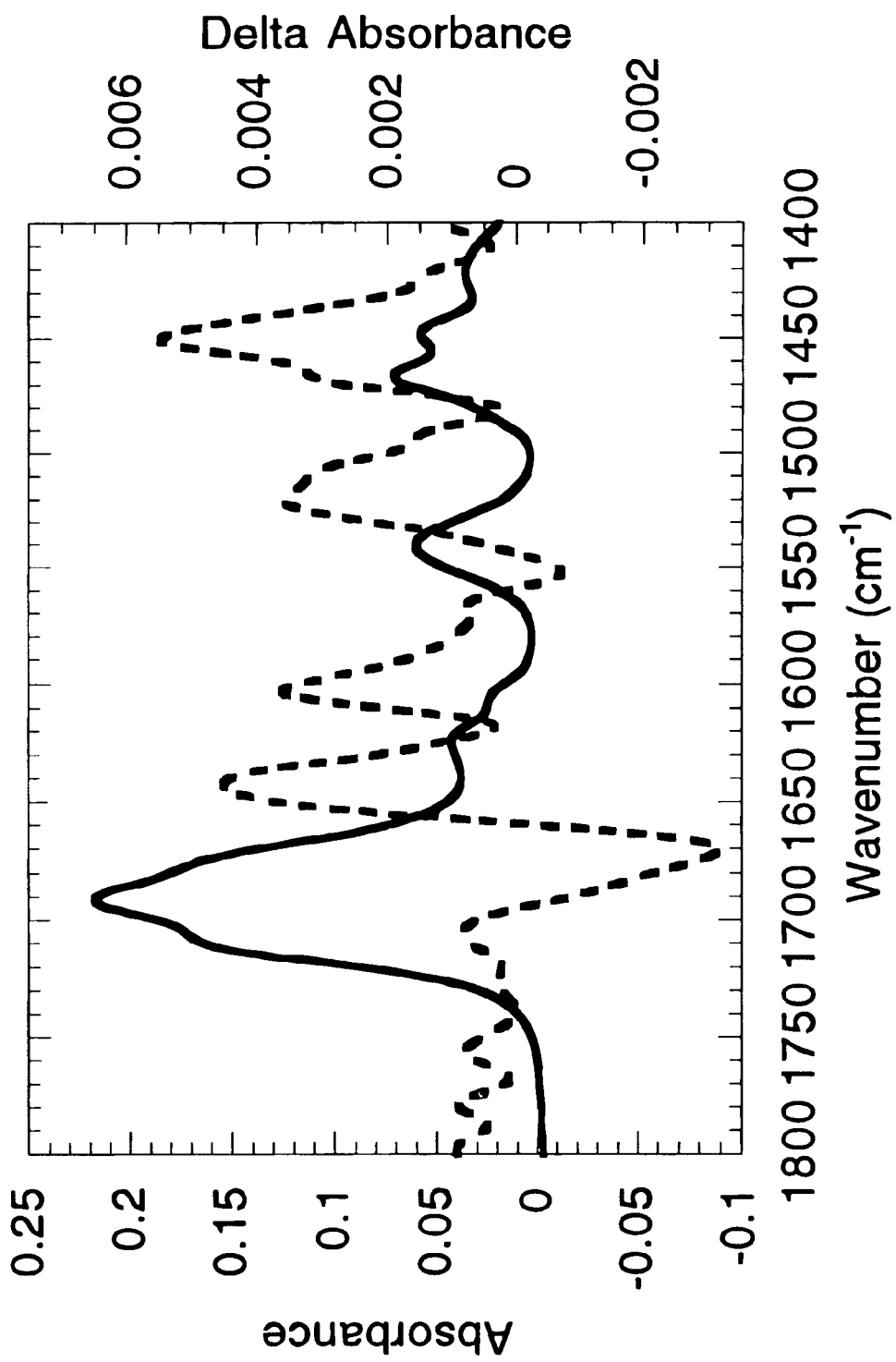
FIG. 13. FTIR scan of compound 5 of FIG. 7.

To gain further insight into the excited-state electronic structure of compound 5 (FIG. 7), time-resolved step-scan FTIR spectroscopy (S$^2$FTIR TRS) with 10 ns time resolution probed the excited state of 5 in CD$_3$CN at room temperature. The ground- and excited-state infrared υ(CO) band energies for 5 are 1679 and 1647 cm$^{-1}$, respectively, as shown in FIG. 13. This substantial negative shift in υ of −31 cm$^{-1}$ is similar in magnitude to other mono-amide derivatized tris-bipyridine complexes such as those containing a propargylamide and ethanolamide. The frequency shift to lower energy for υ(CO) indicates that the MLCT excited-state electron resides on the asymmetrically substituted bipyridine and that significant C=O character is present in the lowest π* excited-state. The relatively large shift in υ(CO) suggests considerable metal-ligand polarization of the MLCT excited state with the receiving orbital localized primarily on the amide-substituted pyridine ring. The metal dπ-ligandπ orbital overlap is also substantial in this complex. Finally, these data are in agreement with previous work with related asymmetrically and symmetrically amide and ester substituted analogs of Ru(bpy)$_3^{2+}$, indicating that on the nanosecond time scale the excited-state electron is localized on the modified bipyridine rather than delocalized over all three ligands or exchanging between the ligands.

Figure 12:
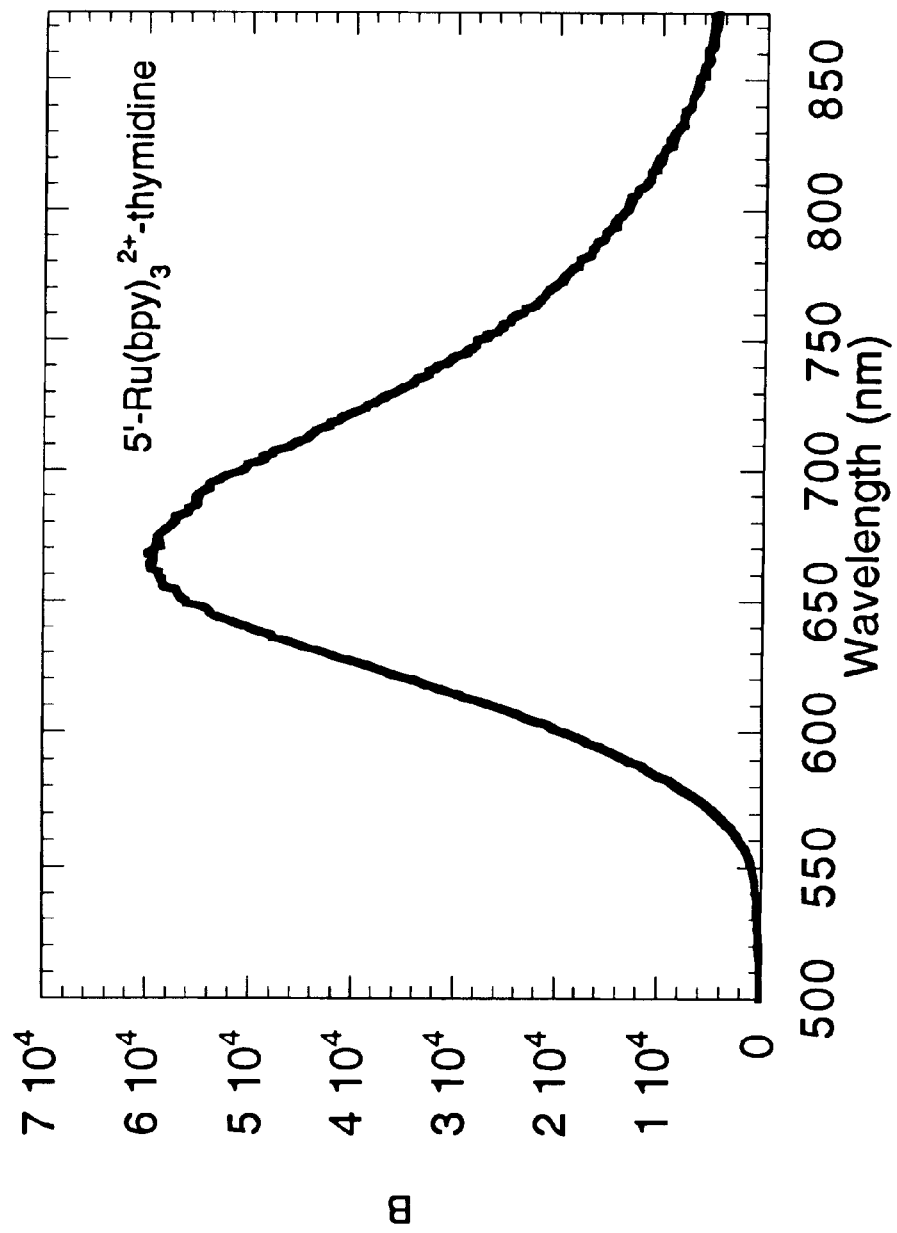
FIG. 12. Excitation and emission spectrum of $Ru(bpy)_3^{2+}$.
Figure 14:
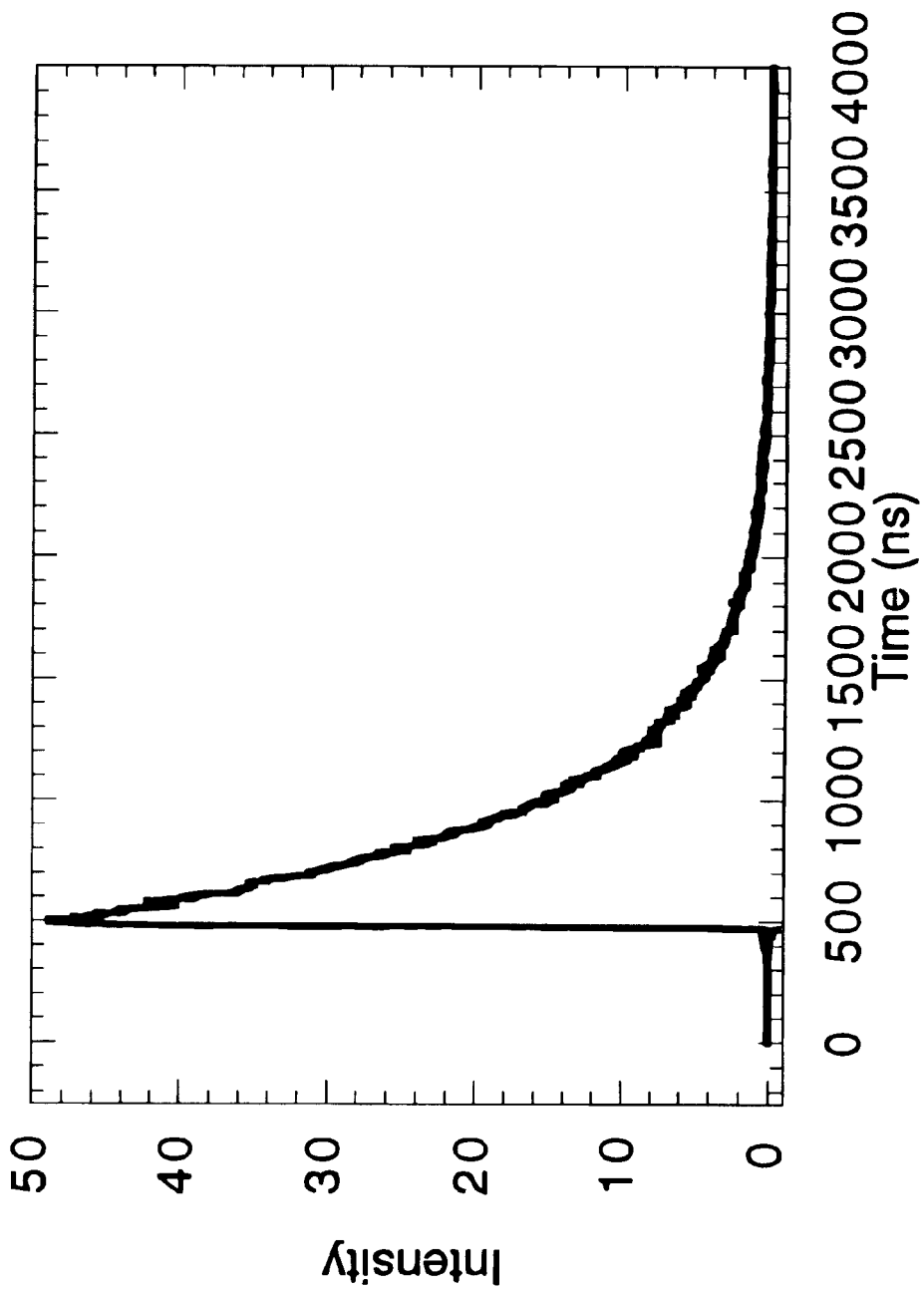
FIG. 14. The emission lifetime spectrum of oligonucleotide duplex, 12•19 (586 ns) at 25° C. in phosphate buffer.

Once compound 5 of FIG. 7 is incorporated in the oligonucleotide, 12, the emission maximum shifts to higher energy (677 nm). The emission maximum is essentially unchanged after hybridization, and the labeled duplex, 12•19, emission is centered at 674 nm (FIG. 12). The emission lifetime of this ruthenium-labeled oligonucleotide, 12, is 572 ns, and that of the modified oligonucleotide duplex, 12•19, is 586 ns at 25° C. in phosphate buffer (FIG. 14). The Ru(diimine)$_3^{2+}$ excited state is not quenched in the presence of DNA and this observation is consistent with the redox potentials of A, C, G, and T.

A ruthenium-oligonucleotide modified surface according to the present invention may be synthesized by first constructing a complementary oligonucleotide single strand, such as 11, to 6 that contains an alkyl amine linker at the 3-terminus. The resulting ruthenium modified duplex (6•11) containing the amino linker may then be annealed, and then anchored to a cyclohexane epoxide derivatized glass slide under basic conditions. Finally, the slide is rinsed with copious amounts of buffer (HEPES 100 mM; pH=7), to afford the surface bound ruthenium-oligonucleotide duplex.

While the above and the following exemplifies the use of uridine, one of ordinary skill will appreciate that other nucleosides, including modified nucleosides, and their corresponding nucleotides (DNA and RNA) may be made and are included within the present invention.

The present invention provides a purine, pyrimidine, nucleoside or nucleotide derivative comprising a detectable marker which is a metal complex containing at least one of a M(diimine)$_x^{y+}$ complex or a metallocene wherein M is a transition metal, and the diimine is selected, for example, from a bipyridine, phenanthroline or terpyridine derivative; x is 1, 2, or 3 and y is 0, 1, 2, 3, or 4, and the bipyridine, phenanthroline, terpyridine or metallocene may be optionally substituted by any one of alkyl (such as $C_1$–$C_8$, linear or branched alkyl), alkene, alkyne, aryl, alkylaryl, carboxyalkyl, amide, ester or ether. The diimines surrounding the metal of the complex may be the same or different. The nucleoside or nucleotide derivatives preferably contain the purine or pyrimidine. The purines of the present invention are selected from natural or synthetic adenine and guanine, or analogs and derivatives thereof which may also include 8-aza-7-deazapurines, and 7-deazapurines. The pyrimidines of the present invention are selected from natural or synthetic cytosine, uracil and thymine, or analogs and derivatives thereof, including 6-azapyrimidines.

In one embodiment, the purine, pyrimidine, nucleoside or nucleotide derivative of the present invention contains a detectable marker containing at least one of a M(diimine)$_2$(diimine)$^{2+}$ complex wherein M is a metal selected from, for example, Fe$^{+2}$, Ru$^{+2}$, Os$^{+2}$, Co$^{+2}$, Rh$^{+2}$, and Cr$^{+2}$ or a M(diimine)$_2$(diimine)$^{3+}$ complex wherein M is a metal selected from, for example, Fe$^{+3}$, Ru$^{3+}$, Os$^{+3}$, Co$^{+3}$, Os$^{+3}$, and Cr$^{+3}$ or a M(terpyridine)$_2^{3+}$ complex wherein M a metal selected from, for example Fe$^{+3}$, Ru$^{+3}$, Os$^{3+}$, Co$^{+2}$, Rh$^{+3}$, and Cr$^{+3}$ or a M(terpyridine)$_2^{2+}$ complex wherein M is a metal selected from, for example, Fe$^{+2}$, Ru$^{+2}$, Os$^{+2}$, Co$^{+2}$, Rh$^{+2}$, and Cr$^{+2}$.

The nucleoside, nucleotide or oligonucleotide, derivative of the present invention is preferably linked to the detectable label or marker through at least one of the 5, 3 or 2 carbon atom of a sugar (ribose, deoxyribose or dideoxyribose) or the 5 carbon of a pyrimidine or the 8 carbon of a purine Preferably, the marker or label is linked through a purine or pyrimidine.

The nucleoside or nucleotide of the present invention is preferably optically active such that the complex is chiral wherein said chirality is fac or ras, R or S, or D or L. Racemic mixtures are also included.

The detectable marker of the present invention is preferably selected from a bis(2,2'-bipyridine)(4'-methyl-2,2'-bipyridine-4-carbonyl propargyl amine) ruthenium (II) substituent; a ferrocene substituent; a bis(2,2'-bipyridine) (4'-methyl-2,2'-bipyridine-4-carbonyl propargyl amine) osmium (II) substituent; and a bis(2,2'-bipyridine) (4' methyl-2,2'-bipyridine-4-carbonyl propargyl amine) rhodium (II) substituent.

An oligonucleotide containing at least one purine, pyrimidine, nucleoside or nucleotide derivative of the present invention is also provided. The oligonucleotide of the present invention optionally contains substitutions, such as sulphur (S), selenium (Se), imino (NH) or boron (B), in the phosphate backbone.

The purine, pyrimidine, nucleoside or nucleotide derivative of the present invention may include a sugar selected from, for example, a ribose, a deoxyribose or a dideoxyribose. The purine, pyrimidine, nucleoside or nucleotide derivative of the present invention may further include any of a dimethoxytritylchloride, α-methyl-6-nitropipronyloxy carbonyl or 2-cyanoethyl N,N'-diisopropylcholoro phosphoramidite derivative and/or a compound of the following structure:

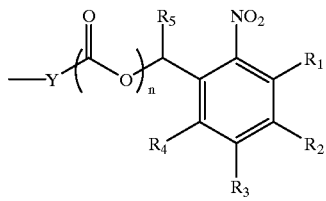

wherein n is either 0 or 1;
Y is an oxygen from a hydroxyl group, such as the 3' or 5' hydroxyl group, of the nucleoside or nucleotide;
$R_1$, $R_2$, $R_3$, and $R_4$ are selected independently from hydrogen, a lower alkyl, alkyl, aryl, benzl, halogen, hydroxyl, alkoxyl, thio, thioether, amino, nitro, carboxyl, formate, formamido, or phosphido or adjacent substituents are substituted oxygen groups that together form a cyclic acetal or ketal; and $R_5$ is selected from hydrogen, alkoxy, alkyl, aryl, halo or alkenyl.

The metal complex of the present invention is preferably covalently bound to a purine or pyrimidine derivative, or nucleobase, in the nucleoside or nucleotide of the present invention. The metal complex is preferably bound through an alkynylamine formed from a terminal alkyne wherein the triple bond may be attached to an amine by a linker moiety of 1–20 atoms. The linker moiety can be straight-chain alkylene, ($C_1$–$C_{20}$ e.g., —$C_3H_6$—), or can contain double bonds (e.g., as in —CCH=CHCH$_2$—), triple bonds (e.g., as in —C=C—CH$_2$—) or aryl groups (e.g., para —$C_6H_4$—, or para—CH$_2$—CH$_2$—$C_6H_3$—). The linker moiety can also contain heteroatoms such as N, O, or S in the chain as part of ether, ester, amine, or amido groups. Suitable substituents on the linker moiety can include $C_1$–$C_6$ alkyl, aryl, ester, ether, amine, amide or chloro groups. Preferably, the linker moiety is a straight-chain alkylene ($C_1$–$C_{10}$); most preferably, the linker moiety is —CH$_2$—. Suitable substituents on the amine are lower alkyl ($C_1$–$C_4$) and protecting groups such as trifluoroacetyl. In general, the amine of the alkynylamine can be primary, secondary or tertiary. For use as a linker, however, the alkynylamine is preferably a primary amine.

In another embodiment, the present invention provides a double-stranded nucleic acid sequence comprising the purine, pyrimidine, nucleoside, nucleotide or oligonucleotide of the present invention and an electron acceptor moiety such as one of Cd, Mg, Cu, Co, Pd, Zn, Fe, Ru and Os. Methods for detecting the transfer of electrons or energy between the electron acceptor and the purine, pyrimidine, nucleoside, nucleotide or oligonucleotide of the present invention are also provided. Detection of the transfer of energy or electrons according to the methods of the present invention may be used to detect the presence or absence of binding of the purine, pyrimidine, nucleoside nucleotide, oligonucleotides, nucleic acids, DNA or RNA of the present invention to a complementary purine, pyrimidine, nucleoside, nucleotide, oligonucleotide, nucleic acid, DNA or RNA in a sample or population. This detection can, in turn, be used to detect, diagnose or treat diseases by means known in the art.

The oligonucleotide, nucleoside or nucleotide of the present invention may be attached to a solid surface which may include or constitute an electrode, nonoparticle, glass, Au, Pt, TiO, ITO, $SnO_2$, silicon, porous silicon, plastic, such as polystyrene, or graphite, for example, attached through one of a covalent bond, an electrostatic association or a hydrogen bond.

The oligonucleotide, nucleoside or nucleotide of the present invention may also contain a further reported group. A reporter can include a chemical group which has a physical or chemical characteristic which can be readily measured or detected by appropriate physical or chemical detector systems or procedures. Ready detectability can be provided by such characteristics as color change, luminescence, fluorescence or radioactivity; or it may be provided by the ability of the reporter to serve as a ligand recognition site to form specific ligand-ligand complexes which contain groups detectable by conventional (e.g., colorimetric, spectrophotometric, fluorometric or radioactive) detection procedures. The ligand-ligand complexes can be in the form of protein-ligand, enzyme-substrate, antibody-antigen, carbohydrate-lectin, protein-cofactor, protein-effector, nucleic acid-nucleic acid or nucleic acid-ligand complexes.

The present invention provides an in vivo, in vitro, or ex vivo method of identifying a nucleic acid molecule or detecting the presence or absence of a nucleic acid molecule which method includes contacting a sample containing or suspected of containing the nucleic acid with a nucleotide, nucleoside, or oligonucleotide of the present invention or a composition containing same, under conditions where said nucleotide, nucleoside, or oligonucleotide can specifically bind to a complementary region of said nucleic acid to form an identifiable complex which may include a double or triple helix, and detecting the binding, preferably by measuring a photophysical, electrochemical, or electron transfer event or alteration, such as an energy or electron transfer to or from the detectable marker of the present invention. The nucleic acid molecule of this method may be synthetic or of human, animal, viral, bacteria, or plant origin.

The electron transfer event detected in the method of the present invention may occur, for example, due to an interaction between two metal complexes on a single nucleic acid strand, an interaction between two metal complexes on separate nucleic acid strands, or an interaction between a metal complex on a single nucleic acid strand and a nucleoside or nucleotide of the present invention. Alternatively, the photophysical alteration or event detected in the method of the present invention may occur due to an interaction between a metal complex and an organic donor/acceptor on a single nucleic acid strand, or an interaction between a metal complex on a single strand and an organic donor/acceptor on a second single nucleic acid strand, wherein the organic donor/acceptor may be selected from, for example, acridine, fluorescein, anthracene, metylphenothiazine, methylviolgen, anthroquione, benzoquione, phenothiazine and quione. The electron transfer event may be, for example, photochemically or electrochemically induced, such as by electrogenerated luminescence.

A method of the present invention includes use of a solid surface containing the oligonucleotide, nucleotide or nucleoside of the present invention attached to the surface and the metal complex donates an electron or energy to the surface or the metal complex accepts an electron or energy from the surface, whereby the detection or identification involves measuring the transfer of the electron or energy. Alternatively, the method of the present invention involves binding the oligonucleotide, nucleotide or nucleoside directly or indirectly to a nucleic acid molecule attached to a surface wherein the metal complex donates an electron or energy to the surface or the metal complex accepts an electron or energy from the surface such that the detection or identification involves measuring the transfer of the electron or energy.

The present invention therefore provides metallo-oligonucleotide derivatives. Specifically, the present invention provides $[(Bpy)_2$ bis(2,2'-bipyridine) (4'-methyl-2,2'bipyridine-4-carbonyl propargyl amine) Ru(II)-2'-deoxyuridine$]^{+2}PF_6^-$, $[(Bpy)_2$ bis(2,2'-bipyridine)(4'-methyl-2,2'bipyridine-4-carbonyl propargyl amine)

Ru(II)-2'-deoxycytidine$]^{+2}2PF_6^-$, $[(Bpy)_2$ bis(2,2''-bipyridine)(4'-methyl-2,2'bipyridine-4-carbonyl propargyl amine) Ru(II)-2'-deoxyadenesine$]^{2+}2PF_6^-$, $[(Bpy)_2$ bis(2,2'-bipyridine)(4'-methyl-2,2'bipyridine-4-carbonyl propargyl amine)

Ru(II)-2 -deoxyguanosine$]^{+2}2PF_6^-$, $[(Bpy)_2$ bis(2,2'-bipyridine)(4'-methyl-2,2'bipyridine-4-carbonyl propargyl amine) Ru(II)-2'-deoxythymidine$]^{+2}2PF_6^-$, $[(Bpy)_2$ bis(2,2'-bipyridine)(4'-methyl-2,2'bipyridine-4-carbonyl propargyl amine) $O_5$ (II)-2-deoxyuridine$]^{+2}$ $2PF_6^-$, $[(Bpy)_2$ bis(2,2'-bipyridine)(4'-methyl-2,2'bipyridine-4-carbonyl propargyl amine) $O_5$ (II)-2-deoxycytidine$]^{+2}$ $2PF_6^-$, $[(Bpy)_2$ bis(2,2'-bipyridine)(4'-methyl-2,2'bipyridine-4-carbonyl propargyl amine) $O_5$ (II)-2-deoxyadenosine$]^{+2}$ $2PF_6^-$, $[(Bpy)_2$ bis(2,2'-bipyridine)(4'-methyl-2,2'bipyridine-4-carbonyl propargyl amine) $O_5$ (II)-2-deoxyguanosine$]^{+2}$ $2PF_6^-$, $[(Bpy)_2$ bis(2,2'-bipyridine)(4'-methyl-2,2'bipyridine-4-carbonyl propargyl amine) $O_5$ (II)-2'-deoxythymidine$]^{+2}$ $2PF_6^-$, Nucleotide, ribose, dideoxy, ferrocene, dimethoxytritylchloride, α-methyl-6-nitropipronyloxy carbonyl and 2-cyanoethyl N,N'-diisopropylcholoro phosphoramidite derivatives, individually or combined, of the above are also provided. Derivatives of the compounds described herein which include a photoremovable or photolabile protecting group, such as are taught in U.S. Pat. No. 5,753,788 are also included in the present invention.

A preferred class of photoremovable protecting groups include aromatic compounds that absorb near-UV and visible radiation, such as are described, for example, in McCray et al., *J. Amer. Chem. Soc.* (1970) 92:6333; and Amit et al.

J. Org. Chem (1974) 39:192. Particularly preferred photo-removable protecting groups include those of the formula

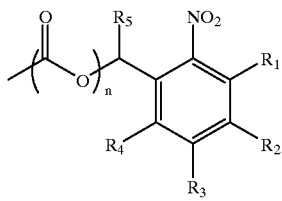

where $R_1$, $R_2$, $R_3$, and $R_4$ independently are a hydrogen atom, a lower alkyl, aryl, benzyl, halogen, hydroxyl, alkoxyl. thio, thioether, amino, nitro, carboxyl, formate, foramino or phosphido group, or adjacent substituents $R_1$–$R_4$ are substituted oxygen groups that together form a cyclic acetal or ketal; $R_5$ is hydrogen, alkoxyl, alkyl, halo, aryl or alkenyl group, and n=0, 1, 2 or 3. Preferred photo-removable protecting groups include the above wherein $R_2$ and $R_3$ together form a methylene acetal, $R_1$ and $R_4$ are hydrogen, $R_5$ is hydrogen or methyl, and n=0 or 1; and the above where $R_2$ and $R_3$ are each a methoxy group, $R_1$ and $R_4$ are each hydrogen, $R_5$ is methyl or hydrogen and n=0 or 1.

The present invention provides oligonucleotide synthesis and nucleic acid sequencing methods which incorporate and utilize the metallo-nucleotides, -nucleosides, -purines or -pyrimidines of the present invention. Synthesis and sequencing methods and techniques are known and described in the art, such as in any of U.S. Pat. Nos. 5,599,695; 5,753,788; 5,047,519; 5,691,146; 5,580,732; and 5,443,791.

Once synthesized, the oligonuceotides of the present invention may be used, for example, as hybridization probes, PCR amplification tools to detect the presence of a specific DNA or RNA, such as in the diagnosis or treatment of disease, to identify specific alleles, to perform tissue typing, to detect genomic sequences in a DNA sample, such asfor forensic DNA analysis (including RFLP analysis or PCR product length distribution) or for diagnosis or treatment of diseases characterized by amplification and/or rearrangement of a characteristic gene.

The metallo-nucleotides of the present invention may be used as probes in oligonucleotides either as bound to a solid support, as part of a solution method or bound to an electrode probe such as, for example, in a method of measuring changes in the rate of electron transfer. One of skill will appreciate that the electron transfer rate of a probe containing a metallo-nucleotide of the present invention will be altered by binding the probe with a complementary nucleic acid sequence. That is, the presence of double stranded nucleic acids, for example, in an oligonucleotide probe assay, can be determined by comparing the rate of electron transfer for the unhybridized probe with the rate for hybridized probes.

The metallo-nucleotides of the present invention may be used as an electron transfer moiety which, when used in conjunction with a second electron transfer moiety, may be used to detect hybridized nucleic acid sequences. Generally, the electron transfer method involves a first nucleic acid single strand which is either modified with two different metallo-nucleotides, or separate modifications are provided on two complementary strands. After hybridization, the sample is excited by a laser, for example, and the rate of photo-induced electron transfer is measured from one metal site to another. Winkler et al., Chem. Rev. 92, 369–379 (1992).

In one embodiment, a single strand of DNA containing two (or more) metallo-nucleic acid bases is synthesized, as described herein. The two metallo-nucleic acid bases on the strand can be located at any site except next to each other. Next, a solution containing single stranded DNA is added. One of the single strands in solution is the target-compliment strand to the modified single strand or metallo-probe strand. The target strand binds to the metallo-probe strand. A photo induced electron-transfer measurement is taken. The difference in the rate of electron transfer between the single strand metallo-probe and the double strand target-metallo probe strand duplex is determined. This difference in electron-transfer signifies that the compliment is bound. As such, this homogeneous method can be used to detect hybridization and used to collect genetic information.

In another embodiment, two single strands of nucleic acids each containing one metallo-nucleic acid base, or nucleotide, are synthesized, as described herein. Next a single strand of nucleic acid is added. The two metallo-probe strands will then bind to the one strand that is the complementary strand to form a duplex. A photo induced electron-transfer measurement is taken. The observation of electron-transfer and measurement of the rate signifies that both metallo-probe strand were bound to the complementary strand. This method can be used to measure and target pieces of DNA.

In yet another embodiment, a single strand of metallo-nucleic acid DNA is synthesized, as described herein and then is attached to a surface. This probe strand is then used to detect a single strand of target complementary nucleic acid. The target strand is modified with a metallo-nucleic acid by means known in the art. The target is then incubated with the probe strand to allow for hybridization and formation of the duplex. The photo induced or electrochemical induced electron-transfer rate is then measured. The detection of the compliment is determined by the change in electron-transfer rate compared to the single probe strand.

A preferred method of the present invention provides for one of the electron transfer moieties being the metallo-nucleotides of the present invention and the other electron transfer moiety being in the form of a solid support, such as an electrode.

In this embodiment, a single stranded nucleic acid probe containing at least one electron transfer moiety is attached via this redox hydrogel to the surface of an electrode. Hybridization of a target sequence can then be measured as a function of conductivity between the electron transfer moiety covalently attached to one end of the nucleic acid and the electrode at the other end. This may be done using equipment and techniques well known in the art, such as those described in the references cited herein.

In similar embodiments, two nucleic acids are utilized as probes as described previously. For example, one nucleic acid is attached to a solid electrode, and the other, with a covalently attached electron transfer moiety, is free in solution. Upon hybridization of a target sequence, the two nucleic acids are aligned such that electron transfer between the electron transfer moiety of the hybridized nucleic acid and the electrode occurs. The electron transfer is detected as outlined above, or by use of amperometric, potentiometric or conductometric electrochemical sensors using techniques well known in the art.

In a further embodiment, a single strand of nucleic acid DNA is synthesized as described above containing a metallo-nucleic acid (metallo-probe strand #1) and then it is attached to an electrode surface (or non-electrode surface). A second single strand of DNA is synthesized as above containing the metallo-nucleic acid (metallo-probe strand #2). An electrode-induced or photoinduced electron-transfer measurement is performed. Both probe strands are then used to detect a single strand of compliment of DNA. The electron-transfer rate is measured from the electrode to the metallo-nucleic acid (or vice versa). The difference in electron-transfer rate compared to the single strand probe and the double stand (target-probe) is determined. Detection of the single strand is confirmed.

In another embodiment, a single strand of DNA containing two metallo-nucleic acids is synthesized as described above. In one of the metallo-nucleic acids, the metal complex is modified to contain a linker between itself and the surface (electrode or non-electrode surface). The target strand is then added and it binds to the compliment. The electron-transfer rate is then measured between the metal complexes and detection of the single strand is determined.

In yet another embodiment, a single strand of DNA containing one metallo-nucleic acid is synthesized as described herein. The metallo-nucleic acid is modified to contain a linker between itself and the surface (electrode or non-electrode surface). The target strand is then added which has been modified to contain a metallo-nucleic acid, and it binds to the compliment. The electron transfer rate is then measured between the metal complexes and detection of the single strand is determined.

In the above detection methods, electron-transfer rates are measured. The ability to detect the single strand is based on the degree or relative change in electron-transfer. Since the electron transfer rate is dependent of the ability to form a DNA duplex, this technique can be used to detect other than perfect compliments. In other words, point mutations, mismatches, substitutions and deletions, where the double stranded nucleic acid is not perfectly matched, will be detectable.

It will also be appreciated that, in the same manner as described above, the detection of a triple helix can be accomplished. In such a method, a single probe strand containing a metallo-nucleic acid is linked to a surface. The target double strand which binds to the single strand is added and triple helix formation is detected by the standard methods described above. Conversely, a probe double strand can be used to detect a single strand of nucleic acid (DNA or RNA).

While this embodiment has been described by reference to a single probe on the surface of an electrode, the present invention also includes formation and use of a multiple array of probes which may be packaged in, for example, a chip such as has been described Pease et al., (PNAS 91, 5022–5026 (May 1994)) and U.S. Pat. Nos. 5,753,788 and 5,599,695 which may be interrogated after hybridization of target or sample sequences by electron transfer rather than fluoresence. The photolabile derivatives of the nucleoside and nucleotides of the present invention are particularly preferred in making these multiple probe arrays. The chip or substrate of this embodiment may be used as a multiple electrode array for detection of hybridization. Alternatively, combinations of electron transfer and fluorescent probes may be used in the method of this embodiment.

A further embodiment of the present invention provides an improved method of labeled nucleic acid polymer synthesis. A preferred method of this embodiment provides use of a purine or pyrimidine, or derivatives thereof, which have been modified, for example, in the C-8 and C-5 positions, respectively, with a group that can be subsequently replaced with a label or reporter group or a detectable marker, such as is described herein or generally known in the art, after nucleic acid polymer synthesis. An alternative method of this embodiment provides modification of nucleotides or nucleosides in the C-2, C-3 or C-5 of the sugar with a group that can be subsequently replaced with a label, reporter or detectable marker. The novel method of the present invention preferably employs standard solid phase chemistry, such as is described, for example, in U.S. Pat. Nos. 5,047, 519; 4,849,513 or 5,428,149; wherein the modified nucleic acid is introduced into an oligonucleotide during synthesis. This embodiment of the present invention provides for coupling of the reporter or labeling group to the nucleoside after synthesis of the nucleic acid polymer or oligonucleotide, while the oligonucleotide is attached to the solid phase, as opposed to conventional methods of adding a labeled nucleotide to the automated synthesis process. While the synthesis method is exemplified herein as being applicable to conventional solid-phase 3' to 5' synthesis, the method may also be applicable in 5' to 3' synthesis, such as is described in Caruthers (U.S. Pat. No. 4,415,732) and/or in chip manufacture, such as in U.S. Pat. Nos. 5,753,788 and 5,599,695.

This improved method of the present invention provides for the direct incorporation of "probes" (labels, reporter groups or detectable markers) into oligonucleotides using solid phase technology. The advantages of this synthetic strategy include: 1) fewer synthetic steps, 2) efficient coupling, 3) ease of purification, and 4) ability to incorporate a wide-range of organic and inorganic probes or reporter groups.

One of skill in the art will appreciate that DNA synthesis may be accomplished as follows. A reactive 3' phosphorous group of one nucleoside is coupled to the 5' hydroxyl of another nucleoside. The former is preferably a monomer, delivered in solution; the latter is preferably immobilized on a solid support. At least three other chemical reactions are necessary to prepare the growing chain of DNA for the next coupling, as described below. In his way, a synthesis cycle is conducted, adding one nucleoside monomer at a time. When the oligonucleotide chain is completed, the crude DNA is cleaved from the support and protecting groups removed from the bases. It is then ready to be desalted or purified and used.

More specifically, for example, the first step of the synthesis cycle is detritylation of a tritylated nucleoside, where the dimethoxytrityl (DMT) group is removed to free the 5' hydroxyl for the coupling reaction. The next step is coupling, in which an activated intermediate is created by simultaneously adding a phosphoramidite nucleoside monomer and for example, tetrazole, or other weak acid. The tetrazole protonates the nitrogen of the phosphoramidite, making it susceptible to nucleophilic attack. The next step, capping, terminates any chains that did not undergo coupling. Since the unreacted chains have a free 5' OH, they can be terminated or capped by acetylation. These unreacted chains become "failure products." C.apping is done, for example, with acetic anhydride and 1-methylinidazole. Since the chains that reacted with the phosphoramidite in the previous step are still blocked with the dimethoxytrityl group, they are not affected by this step. Although capping is not absolutely required for DNA synthesis, it minimizes the length of impurities, making it possible to do post-synthesis trityl-selective purification of the final product. Finally, the internucleotide linkage is converted from the phosphite to the more stable phosphotriester by oxidation with an iodine solution. For the synthesis of phosphorothioate oligonucleotides, the internucleotide phosphite is sulfurized between coupling and capping. After oxidation, the DMT group is removed with trichloroacetic acid and the cycle repeated until chain elongation is complete. At this point, the oligonucleotide is cleaved from the solid support with concentrated ammonium hydroxide. Ammonia treatment also removes the cyanoethyl phosphate protecting groups. The crude DNA in ammonium hydroxide solution is then heated to remove the protecting groups on the exocyclic anines of the bases.

The improved method of the present invention involves addition of at least one halodonucleoside (where halo may be any of fluorine, chlorine iodine or bromine, such as any of fluorouridine, fluoroadenosine, fluoroguanosine, fluorocytidine, fluorothymidine, chlorouridine, chloroadenosine, chloroguanosine, chlorocytidine, chlorothyrnidine, iodouridine, iodoadenosine, iodoguanosine, iodocytidine, iodothymidine, bromouridine, bromoadenosine, bromoguanosine, bromocytidine and bromothymidine) into the growing oligonucleotide during synthesis, with subsequent attachment of a reporter group to same through Pd(O) or other metal mediated reaction forming a C—C bond, such as a Heck or Sonogashira reaction either prior to or subsequent to removal of the oligonucleotide from the solid support. In this way, the improved method of the present invention allows for synthesis of labeled oligonucleotides without the need for using labeled nucleosides during the oligonucleotide synthesis process. The present invention provides therefore an improved method of oligonucleotide synthesis which includes combining, for example, phosphoramidite nucleoside derivatives in combination with a solid support wherein the improvement includes adding at least one phosphoramidite halonucleoside during the synthesis and subsequently labeling the halonucleoside with a marker in a metal catalyzed reaction.

A preferred means of introducing the detectable labels of the present invention involve the use of halodonucleoside intermediates, such as are described U.S. Pat. No. 5,047,519, which may be incorporated in automated and manual oligonucleotide synthesis techniques. One common method of introducing a side chain to a nucleic acid involves the use of palladium and mercury. This acetoxymercuration reaction was developed for introducing covalently bound mercury atoms into the 5-position of the pyrimidine ring, the C-8 position of the purine ring or the C-7 position of a 7-deazapurine ring, of nucleotides. Organomercurial compounds would then react with an olifinic compound in the presence of a palladium catalyst to form a new carbon-carbon bond. The palladium coupling reaction, or Heck reaction, has been previously used to construct carbon-carbon bonds as described in *JACS* 1968, 90, 5518; *JACS* 1968, 90, 5526; *JACS* 1968, 90, 5531; *JACS* 1968, 90, 5535; and *JACS* 1969, 91, 6707. The use of this reaction in modified nucleic acid synthesis is described in *PNAS*, 1973, 70, 2238; *Biochem*. 1975, 14, 2447; *JACS*, 1978, 100, 8106; and *JACS* 1980, 102, 2033. This procedure is performed in solution with the mercurial labeled nucleic acid and a palladium catalyst. However, the use of mercury and the purification procedures make this methodology unfavorable, although extensively used. A number of nucleotide analogs that contain potential organic and inorganic probe ligands covalently attached to the C-5 pyrimidine ring that can be a used as an affinity reagent have been synthesized to exemplify this improved method. Accordingly, this improved method has included the synthesis, and characterization of organic and inorganic labeled derivatives of 5'-deoxyuridine, and their direct incorporation into an oligonucleotide on solid support using the Heck reaction.

The C-5 position of deoxyuridine, for example, has been the target of extensive modifications. When incorporated into duplex DNA such modifications are located in the major groove, and as such do not disrupt Watson-Crick base pairing. These C-5 deoxyuridine analogs, for example, can be incorporated into a DNA oligomer using solid phase synthesis and standard phosphoramidite chemistry, as exemplified herein. Modification of the sugar of nucleosides and nucleotides, as described and exemplified herein, may also provide advantages.

One application of modified nucleic acids involves the use of sequence specific antisense or antigene oligonucleotides to control gene expression. This is a promising approach to treating a range of diseases that include viral infection and cancers. In recent years considerable efforts have been invested in the synthesis of chemically modified oligonucleotides to improve nuclease stability, target binding affinity and cellular uptake properties.

The present invention provides an improved method of oligonucleotide synthesis therefore which includes attaching a 3' nucleoside, such as any of adenosine, guanosine, cytidine or uridine, of the oligonucleotide to be synthesized to a solid support through a labile linker arm, preferably an acid- or base-labile linker arm, such as a phosphoramidite derivative. The nucleotide preferably includes a di-p-ansylphenylmethyl (or dimthoxytrityl) group on the 5' carbon of the sugar, such as ribose or deoxyribose, as is commonly used in automated oligonucleotide systems.

The improvement of the presently disclosed method includes incorporating at least one nucleotide containing at least one halonucleoside into the oligonucleotide during the automated or manual synthesis method followed by attaching a detectable marker to the at least one nucleotide through, preferably, an alkynylamine group. Preferably, the iodo- or bromo-nucleoside is a 5-iodo- or 5-bromo-pyrimidine or 7-iodo- or 7-bromo-purine. 7-deazapurines, 8-aza-7-deazapurines and 6-azapyrimidines may also be used. The labeled alkynylamino-nucleotides of this aspect of the present invention are preferably prepared through a palladium catalyzed reaction.

The palladium catalyzed reaction is preferably carried out in the presence of a Cu(I) co-catalyst. Suitable palladium catalysts include Pd(0) complexes, for example, tetrakis (triarylphosphine)Pd(0). The amount of Pd catalyst used is generally 1–25 mol % (based on the iodonucleoside), preferably 5–15 mol %. The mole ratio of Cu(I) co-catalyst to Pd(0) catalyst is more than 1 but less than 20.

The following Examples serve to more fully describe the manner of using the above-described invention. It is understood that these examples in no way serve to limit the scope if this invention, but rather are presented for illustrative purposes. Unless defined otherwise, the following abbreviations have been used herein: MLCT is Metal to ligand charge transfer; HEPES is 4-(2-hydroxyethyl)-1-piperazinrrthanesulfonic acid; HOBt is 1-hydroxybenzotriazole; DIPEA is N,N-diisopropylethylamine; DMF is N,N-dimethylformamide; TEA is triethylamine; DMT is dimethoxytrityl; FPAU is Ferrocene parpagyl amide uridine; MsCl is methanesulfonyl chloride; CDI is carbonyldiimidozole; LH-20 is Sephadex LH$_{20}$ resin; DIPEA is N,N-diisopropylethylamine; DCC is dicyclohexylcarbodiimide; HPLC is High Pressure Liquid Chromatography; FAB-MS is Fast atom bondarment mass spectrometry; TEAA is triethylamine acetate; MALDI is Matrix Assisted Laser Desorption Ionization-time of flight mass spectoscopy; Tm is melting temperature; 4-m-4'-ca-bpy is 2,2'-bipyridine=bpy; 4-Methyl-2,2'-bipyridine-4'- carboxylic acid; M.W. is molecular weight; EDTA is Ethylenediaminetetraacetic acid; B-DNA is B-form DNA; CDI is carbonyl diimidazole; ODN is Oligonucleotide; ACN is acetonitrile; ITO is indium tin oxide; and DCU is dicyclohexylcarbodiimide.

EXAMPLE 1

5-Iodo-2'-deoxyurdine and benzoyl chloride were dissolved in dry pyridine and stirred at room temperature for overnight. The solvent was then removed by vacuum distillation and the resulting yellow oil was dissolved in ethyl acetate, washed with 5% sodium bicarbonate, 0.5 M HCl, water and the solution was then dried over sodium sulfate. The solvent was removed by rotary evaporator and the crude product was purified on a silica gel column (in 2% MeOH/ $CHCl_3$) in 20% hexane/chloroform. FAB-MS: molecular weight of 562; NMR peaks are consistent with the structure.

EXAMPLE 2

Ferrocene monocarboxylic acid, propargylamine HCl, HOBt and TEA were dissolved in DMF/DCM at 0° C. DCC was dissolved in DMF and than added dropwise to the reaction mixture. The mixture was stirred and allowed to reach room temperature overnight. Solvent was next removed by vacuum distillation. The solid ws then dissolved in ethyl acetate, and DCU was removed by filtration. The ethyl acetate solution was washed with $NaHCO_3$(5%),0.5 N HCl, brine and $H_2O$ and dried over sodium sulfate. Solvent removed by rotary evaporation. Product purified FAB-MS: M.W. 269, 1; NMR peaks are consistent with the structure.

EXAMPLE 3

FPA, 5-iodo-3',5dibenzolyloxy-2'-deoxyuridine, $(PPh_3)_4Pd(0)$ and CuI were dissolved in dry DMF, and then TEA added to the mixture. The reaction mixture was stirred for 6 hours at room temp. The solvent was next removed by vacuum distillation, and chloroform was added. This mixture was then washed with 10% EDTA, water and dried over sodium sulfate and solvent removed by rot. evap. An orange oil dissolved in the chloroform which was subsequently crashed out of hexane. The solid compound was purified further on silica gel column (in 2% MeOH/chloroform). FAB-MS: molecular weight of compound expected to be 701; mass spectrum shown peak at 805. NMR: characteristic peaks of FPA and uridine moieties.

EXAMPLE 4

The orange FPAU was dissolved in methanolic ammonia solution and allowed to react for 48 hours. The solvent was removed by rotary evaporation. A solid was washed with ether and dried on high vacuum. FAB-MS: molecular weight 492,9, NMR assigned.

EXAMPLE 5

Deprotected FPAU was dissolved n dry pyridine and the solvent was removed by vacuum distillation. This process was repeated 2 times. Finally the FPAU was dissolved in dry pyridine and dimethoxytrityl chloride (DMT-Cl) was added to the flask. The mixture ws stirred at room temperature under nitrogen overnight.

Methanol was then added to the reaction mixture to consume and excess DMT-Cl. The solvent was removed by high vac. A solid was then dissolved in $CHCl_3$ and crashed out of ether. FAB-MS: molecular ion peak of 795.3, NMR assigned.

EXAMPLE 6

The DMT-FPAU was dissolved in dry acetonitrile and diisopropylethylamine and 2-cyanoethylchloro-N,N-diisopropylphosphramidite was added dropwise. The reaction mixture was stirred under $N_2$ for 4 hours. The reaction mixture was then added dropwise to a stirring ether solution and a precipitate formed. The solid was dried on KOH pellets under high vacuum. The sample was then used in a DNA synthesizer without further purification.

EXAMPLE 7

4'-Methyl-2,2'-bipyridine-4-carboxylic acid, propargylamine hydrochloride, HOBt and TEA dissolved in DMF 0° C. DCC was dissolved in DMF and added dropwise to the reaction mixture. The mixture was stirred at room temperature overnight. Solvent was removed by vacuum distillation. The solid compound was dissolved in ethyl acetate and DCU was removed by filtration. The ethyl acetate solution was washed with $NaHCO_3$(5%), 0.5 N HCl, brine and dried over sodium sulfate. Solvent was removed by rot. evap. and the compound was purified by column chromatography using 2% methanol in chloroform as eluent. FAB-MS: M.W. 25 1[M+]; NMR assigned.

EXAMPLE 8

$Rubpy_2Cl_2$ and 4'-methyl-2',2'-bipyridine-4-carbonyl propargyl amine were suspended in 70% ethanol and refluxed for 10 hours. Reaction mixture was cooled and ethanol was removed. The water solution after standing for 4 hours at room temperature, the mixture was filtered and the solid compound washed with cold water. In filtrate, a saturate aqueous solution $NH_4PF_6$ was added until no further ppt. was observed and the mixture was kept at room temperature for 2 hours and then filtered, washed with cold water, ether and dried overnight to get pure orange color compound.

EXAMPLE 9

Bis(2,2'bipyridine)(4'-methyl-2,2'-bipyridine-4-carbonylpropargyl amine) ruthenium(II), 5-iodo-3',5'-dibenzoyloxy-2'-deoxyuridine, $(PPh_3)_4Pd(0)$, and CuI were dissolved in dry DMF, and TEA was added to mixture. The reaction mixture was stirred for 8 hours at room temp. The solvent was removed by vacuum distillation keeping the temperature less than 45° C. The orange oil was dissolved in dry acetonitrile and precipitated by added dry ether. The orange compound was filtered and washed with dry ether and dried over KOH pellets at high vacuum. FAB-MS: 1989. NMR: assigned.

EXAMPLE 10

The $[(bpy)_2(bpy-N-propargyl)Ru(II)-3',5'-dibenzolyloxy-2'-deoxy\ uridine]\ 2PF_{6-}$ was dissolved in methanolic ammonia solution and left for 48 hours with occasional shaking. The solvent was removed by rotary evaporation. A orange solid compound was dissolved in dry $CH_3CN$ and added dropwise to an ether solution. The product was precipitated, filtered and dried over KOH pellets under high vacuum. FAB-MS: MW 1181 ($M^+$-$2PF_6^-$ 891, M+-$PF_6^-$ 1036.) NMR: assigned.

EXAMPLE 11

The $[(bpy)_2(bpy-N-propargyl)Ru(II)-2'-deoxy\ uridine]$ $2PF_6^-$ was dissolved in dry pyridine and the solvent was removed by vacuum distillation. This process was repeated 2 times. Finally the compound was dissolved in dry pyridine and dimethoxytrityl chloride (DMT-Cl) was added to the flask. The mixture was stirred overnight at room temperature under nitrogen. Methanol was added to the reaction mixture to consume any excess DMT-Cl. The solvent was then removed under high vacuum. An orange solid was then dissolved n $CH_3CN$ and precipitated with ether. The product was dried over KOH pellets under high vacuum. FAB-MS: MW 1402; ($M^+$-$2PF_6^-$ 1192); NMR assigned.

EXAMPLE 12

The [$(bpy)_2$(bpy-N-propargyl)Ru(II)-5'-DMT-2'-deoxy uridine] $2PF_6^-$ was dissolved in dry ACN and diisopropylethylamine was added to flask followed by slow addition of 2-cyanoethylchloro-N,N-diisopropylphosphramidite under argon. The reaction mixture was stirred for 8 hours under argon and solvent evaporated under vacuum. The orange solid compound, thus obtained, was dissolved in $CH_3CN$, precipitated with dry ether and dried over KOH pellets under high vacuum. The sample was then used in a DNA synthesizer without further purification. FAB-MS MW 1683 ($M^+$-2PF6-) NMR assigned

EXAMPLE 13

Bis(2,2'-bipyridine)(4'-methyl-2,2'-bipyridine-4-carbonyl propargyl amine) osmium(II), 5-iodo-3',5'-dibenzoyloxy-2'-deoxyuridine, $(PPh_3)_4Pd(0)$, and CuI were dissolved in dry DMF, and TEA was added to mixture. The reaction mixture was stirred for 8 hours at room temp. The solvent removed by vacuum distillation keeping the temperature less than 45° C. The green oil was dissolved in dry acetonitrile and precipitated by adding dry ether. The orange compound was filtered and washed with dry ether and dried over KOH pellets at high vacuum.

EXAMPLE 14

The [$(bpy)_2$(bpy-N-propargyl)Os(II)-3 ',5'-dibenzoyloxy-2'-deoxy uridine] $2PF_6$- was dissolved in methanolic ammonia solution and left for 48 hours with occasional shaking. The solvent was removed by rotary evaporation. A green solid compound was dissolved in dry $CH_3CN$ and added dropwise to an ether solution. The product was precipitated, filtered and dried over KOH pellets under high vacuum.

EXAMPLE 15

[$(Bpy)_2$(bpy-N-propargyl)Os(II)-2'-deoxy uridine] $2PF_6$- was dissolved in dry pyridine and the solvent was removed by vacuum distillation. This process was repeated 2 times. Finally the compound was dissolved in dry pyridine and dimethoxytrityl chloride (DMT-Cl) was added to the flask. The mixture was stirred overnight at room temperature under nitrogen. Methanol was added to the reaction mixture to consume any excess DMT-Cl. The solvent was then removed under high vacuum. An green solid was then dissolved in $CH_3CN$ and precipitated with ether. The product was dried over KOH pellets under high vacuum.

EXAMPLE 16

The [$(bpy)_2$(bpy-N-propargyl)Os(II)-5'-DMT-2'-deoxy uridine] $2PF_6$- was dissolved in dry ACN and diisopropylethylamine was added to flask followed by slow addition of 2-cyanoethylchloro-N,N-diisopropylphosphramidite under argon. The reaction mixture was stirred for 8 hours under argon and solvent evaporated under vacuum. The green solid compound, thus obtained, was dissolved in $CH_3CN$, precipitated with dry ether and dried over KOH pellets under high vacuum.

EXAMPLE 17

The oligonucleotides shown in Table 1 were synthesized from the 3' to 5' end on both the 0.2 and 1.0 μmol scale using standard automated DNA synthesis on an ABI 395 DNA/RNA synthesizer and standard reagents purchased from Glen Research. A 0.1 M solution of ruthenium-labeled 5'-dimethoxytrityl-3'-(2-cyanoethyl-N,N-diisopropyl) phosphoramidite-2'-deoxyuridine in dry acteonitrile was prepared with DMT-ON and end protection protocol except that the reaction time for the modified phosphoramidite was increased. After synthesis the oligonucleotide was collected in a vial and incubated at 55° C. in $NH_3$ overnight to completely deprotect the oligonucleotide. Collection and analysis of the DMT fractions during automated synthesis showed efficient phosphoramidite coupling (>95%) for the unmodified oligonucleotides (9–11) and until the ruthenium-labeled nucleoside phosphoramidite was added. The coupling of the ruthenium nucleoside phosphoramidite occurred at ≈40%, and additional couplings after incorporation of this modified nucleoside were high (>95%).

EXAMPLE 18

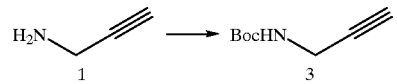

Propargyl amine hydrocloride(0.92 g, 10 mmol) was dissolved in water (15 ml) and $NaHCO_3$ (0.84 g, 10 mmol) was added and stirred. Di-t-butyl dicarbonate (2.18 g, 10 mmol) was dissolved in $CHCl_3$ (20 ml) and added dropwise. The reaction mixture was stirred for 3 hr and the $CHCl_3$ layer was separated, and the water phase was further extracted with $CHCl_3$. We subsequently combined the $CHCl_3$ layers and washed with water, dried over $Na_2SO_4$, and concentrated to give 1.35 g (87%) as oil, which crystallized on standing at −4° C. Mass Spect. (FAB) MW 155 [M+]; NMR assigned Haralambidis, J.; Cbai, M.; Treager, G. W. Nucleic Acid Res. 1987, 15, 4857–4876

EXAMPLE 19

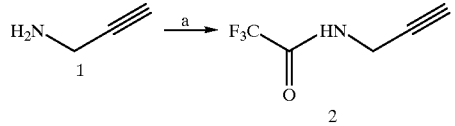

Propargyl amine (1.03 ml, 15 mmol) was dissolved in dry THF (15 ml) and cooled to 0° C. Trifluoroacetic anhydride (2.8 g, 20 mmol) was added dropwise and the reaction mixture was stirred for 3 hrs. Water(20 ml) was then added to reaction mixture and extracted with ether. The ether layer was washed with water, dried over $Na_2SO_4$, and concentrated to give a dark color oil 2.2 g (82%). Mass Spect. (FAB) MW 152 [M+]; NMR assigned. Cruickshank, K. A.; Stockwell, D. L. Tetrahedron Lett. 1988, 29, 5221–5224

EXAMPLE 20

6-(((6-((Biotinoyl)amino)hexanoyl)amino)hexanoyl propargyl amine

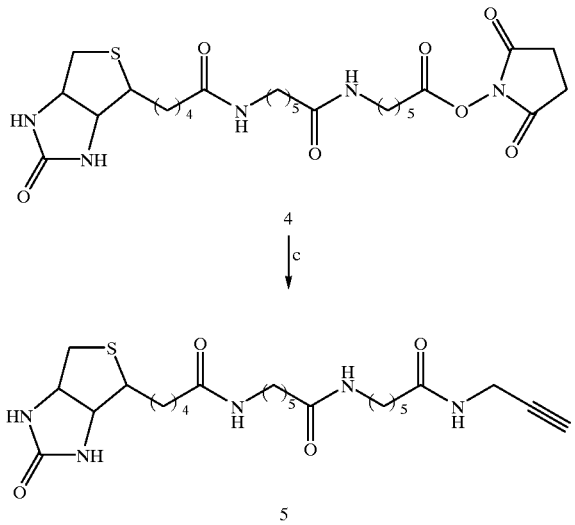

To a stirred solution of 6-((6-((Biotinoyl)amino) hexanoyl)amino)hexanoic acid, succinimidyl ester (biotin-NHS ester) (0.2 g, 0.35 mmol) in dry DMF (5 ml), propargyl amine (0.04 ml, 0.6 mmol) was added. A white precipitate formed within 15 min and the mixture was stirred overnight. The solvent was removed in vacuo and the compound was dissolved in CHCl$_3$. Next the CHCl$_3$ was slowly added to a stirred solution of hexane, forming a white precipitate, which on drying afforded 0.15 g (83%). Mass Spect. (FAB) MW 508 [M+]; NMR assigned. Crisp, G. T.; Gore, J. Syn. Comm. 1997, 27, 2203–2125

EXAMPLE 21

4'-Methyl-2,2'-bipyridine-4-carboxaldehyde

A solution of 4,4'-dimethyl-2,2'-bipyridine (5.27 g, 28.6 mmol) in dioxane (150 ml), SeO$_2$ (3.48 g, 31.4 mmol) was added and refluxed for 24 hr with stirring and filtered hot. The dioxane was removed by rotary evaporator, and the residue was dissolved in ethylacetate and filtered to remove additional solid material. The ethylacetate layer was then extracted with 1M Na$_2$CO$_3$ (2*100 ml) to remove additional carboxylic acid and 0.3M Na$_2$S$_2$O$_5$(3*100 ml) to form the aldehyde bisulfite. The combined aquous extracts were adjusted to pH 10 with Na$_2$CO$_3$ and extract with DCM (4*100 ml). Evaporation of solvent to get 1.9 g (33%) pure white solid compound. Mass Spect. (FAB) MW 199 [M+]; NMR assigned.

EXAMPLE 22

4'-Methyl-2,2'-bipyridine-4-carboxylic acid

A suspension of 4'-methyl-2,2'-bipyridine-4-carboxaldehyde (3.5 g, 15 mmol) in 95% EtOH (150 ml) was added a solution of AgNO$_3$ (3.15 g) in water (32 ml). The suspension was stirred rapidly and 1M NaOH (79 ml) solution was added dropwise over 20 min to form Ag$_2$O. The dark black solution was stirred for an additional 15 hrs. EtOH was removed by rotary evaporator and filtred to remove Ag$_2$O and unreacted metallic Ag. The residue was washed with 1.3M NaOH (2*20 ml) and H$_2$O 20 ml. The combined basic filterate was extracted with DCM to remove unreacted aldehyde and adjusted to pH 3.5 with 1:1(v/v) 4N HCl/AcOH to afford white compound. After keeping overnight at −10° C. the compound was collected and dried to afford pure compound 2.9 g (77%). Mass Spect. (FAB) MW 215 [M+]; NMR assigned.

EXAMPLE 23

4'-Methyl-2,2'-bipyridine-4-carbonyl propargyl amine

4'-Methyl-2,2'-bipyridine-4-carboxylic acid (0.22 g, 1 mmol), propargylamine hydrochloride (0.092 g, 1 mmol), HOBt (0.15 g, 1 mmol) and DIPEA (0.21 ml) were dissolved in dry DMF (15 ml) and cooled to 0° C. DCC (0.25 g, 1.2 mmol) was dissolved in DMF (3 ml) and added dropwise to the reaction mixture. The mixture was stirred at room temperature overnight. DCU was filtered off and solvent was removed by vacuum distillation. The remaining solid compound was dissolved in ethyl acetate and washed with NaHCO$_3$(5%), 0.5 N HCl, brine and dried over sodium sulfate. Solvent was removed by rotary evaporator and the compound was purified by column chromatography using 2% methanol in chloroform as eluent afforded 0. 19 g (76%). FAB-MS: M.W. 251 [M+]; NMR assigned.

EXAMPLE 24

Bis(2,2'-bipyridine)(4'-Methyl-2,2'-bipyridine-4-carbonypropargylamine)ruthenium(II) bis (hexafluorophosphate)

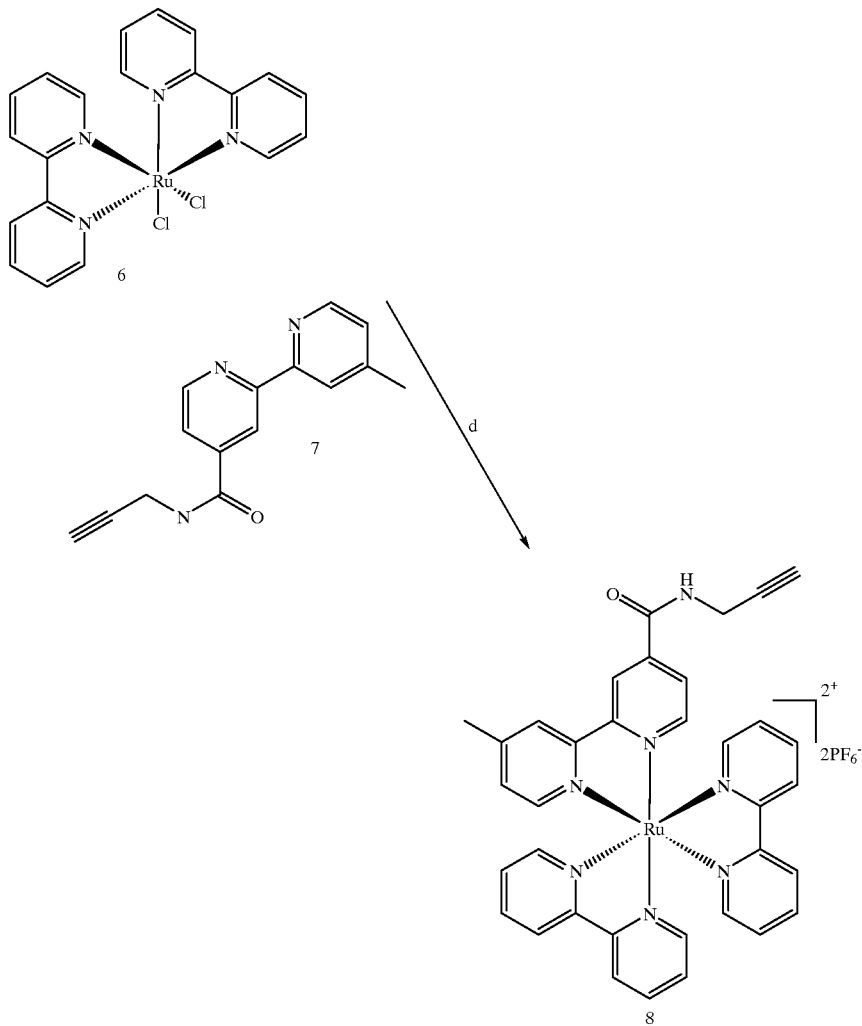

The compound 4'-methyl-2',2'-bipyridine-4-carbonyl propargyl amine (0.08 g, 0.3 mmol) in 70% ethanol/H$_2$O (25 ml) was added Ru(bpy)$_2$Cl$_2$(0.15 g, 0.3 mmol) and refluxed for 10 hr. The reaction mixture was cooled and ethanol was removed in vacuo. The solution after standing for 4 hours at room temperature, was filtered and the solid compound washed with cold water. A saturated aqueous solution of NH$_4$PF$_6$ was added until no further ppt. was observed and the mixture was kept at room temperature for 2 hours and then finally filtered, washed with cold water, ether and dried overnight to get pure orange colour compound 0.45 g (82%). Mass Spect. (FAB) MW 809 [M++PF6]; NMR assigned.

EXAMPLE 25

Bis(2,2'-bipyridine)(4'-Methyl-2,2'-bipyridine-4-carbonypropargylamine)osmium(II) bis (hexafluorophosphate)

Solid Os(bpy)$_2$Cl$_2$ (0.12 g, 0.2 mmol) and 4'-methyl-2', 2'-bipyridine-4-carbonyl propargyl amine (0.08 g, 0.3 mmol) were suspended in 70% ethanol/H$_2$O (50 mi) and refluxed for 10 hr. The reaction mixture was cooled and ethanol was removed. The water solution after standing for 4 hours at room temperature, was filtered and the solid compound washed with cold water. In filterate, a saturated aqueous solution of NH$_4$PF$_6$ was added until no further ppt. was observed and the mixture was kept at room temperature for 2 hours and then filtered, washed with cold water, ether and dried overnight to get pure black colour compound 0.25 g (76%). Mass Spect. (FAB) MW 898 [M++PF6]; NMR assigned.

EXAMPLE 26

5'-O-(4,4'-Dimethoxytrityl)-2'-deoxy-5-iodo uridine

2'-Deoxy-5-iodo uridine (1.1 g, 3 mmol) was dissolved in dry pyridine (5 ml) and the solvent was removed on high vacuum. This process was repeated two times. Finally the compound was dissolved in dry pyridine (15 ml) and dimethoxytrityl chloride (DMT-Cl) (1.4 g, 3.5 mmol) was added to the flask in two portion. The mixture was stirred for 4 hr at room temperature. Methanol was added to the reaction mixture to consume any excess DMT-Cl. The solvent was then removed and the compound was dissolved in CHCl$_3$ and washed with 5% NaHCO$_3$ and finally with water and dried over Na$_2$SO$_4$ and concentrated to get crude product. Purification by flash column chromatography afforded white pure compound 1.7 g (85%). Product was dried over KOH pellets under high vacuum. Mass Spect. (FAB) MW 641 [M+]; NMR assigned.

EXAMPLE 27

5'-O-(4,4'-Dimethoxytrityl)-3'-O-(2-cyanoethyl)-N, N'-diisopropylphosphoramidite-2'-deoxy-5-iodo uridine 5'-O-(4,4'-Dimethoxytrityl)-2'-deoxy-5-iodo uridine (1.28 g, 2 mmol) was dissolved in dry DCM (40 ml) and diisopropylethylamine (0.7 ml, 4 mmol) was added to flask and cooled in ice bath. Next, 2-cyanoethylchloro-N,N-diisopropylphosphoramidite (0.7 ml, 3 mmol) was added slowly under nitrogen. The reaction mixture was stirred for 2 hours under argon and then DCM (10 ml) was added. The solvent was removed and the compound was dissolved in CHCl3 and washed with 5% $NaHCO_3$, water, dried over $Na_2SO_4$, and concentrated to give the product 1.5 g (89%). The compound was used as such without further purification after drying over KOH pellets under vacuum. Mass Spect. (FAB) MW 842 [M++PF6]; NMR assigned.

EXAMPLE 28

Synthesis of Oligonucleotide

The ODN were synthesized from 5' to 3' end on a 0.2 and 1 μmol scale. The 0.1M solution of dried monomer iodouridine phosphoramidite was prepared in anhydrous acetonitrile. Synthesizer bottle number 5 was filled with 5'-dimethoxytrityl-3'-(cyanoethyl-N-diisopropyl) phosphoramidite-2'-deoxy-5-iodouridine and manually diluted with dry acetonitrile to give a concentration 0.1M. Solid-phase synthesis was then preformed in such a way that the sequence was stopped after incorporation of the iodouridine, but keeping the DMT-ON and with no end deprotection from the resin. The column was taken out from the synthesizer and dried over $N_2$ thus maintaining the anhydrous condition. Next, the column cap was opened and the coupling compound, side chain, catalyst $(PdPh_3P)_4$, copper iodide were added and dried with $N_2$ for 30 minutes. All addition were carried out under $N_2$ atmosphere. 250 ml of dry DMF: $Et_3N(3.5:1.5)$ solution was added and cap of the column closed. The column was placed on a shaker for 3 hrs. When the reaction completed, the column was washed with DMF:$Et_3N$ (9:1), acetonitrile (40 ml), dried with $N_2$ for 30 min, and reinstalled on the synthesizer and additional DNA bases were added.

Collection and analysis of the trityl fractions during automated synthesis showed efficient phosphoramidite coupling throughout the procedure, with both the standard pyrimidine and purine nucleosides as well as with 5-iodo-uridine (>95% ). Finally, the modified oligonucleotide was collected and incubated at 55° C. in $NH_3$ overnight, to completely deprotect the oligonucleotide.

Analysis of the HPLC traces of the crude oligonucleotide products showed efficient Pd(0) cross-coupling reactions for each functional group (yields ranged from 85 to 92%). Enzymatic digestion of the modified oligonucleotides showed selective coupling to 5-iodouridine with no side reactions observed with the other bases. Of the groups synthesized, the type, size, 3-dimensional shape, or charge of the functional group did not significantly affect the Pd(0) cross-coupling reaction nor the ability to synthesize both short and long modified oligonucleotides. The mass spectrum of each sequence was observed using either FAB or MALDI.

The following sequences were synthesized (5'-3'):

```
 1) DMT-TU*G CA
 2) DMT-TU*C A
 3) GTT U*GA
 4) CTU* AGC A
 5) TCA ACAGTTTGU*AGCA(SEQ ID NO:17)
 6) TCAACAGTTTGU*AGC A(SEQ ID NO:18)
 7) TGCTACAAACTGU*TG A(SEQ ID NO:19)
 8) TGCTACAAACTGU*TG A(SEQ ID NO:20)
 9) TACATCCTAU*CT(SEQ ID NO:21)
10) GGTCTTATTCACCACAATAACCTCAGTU*CT(SEQ ID NO:22)
11) DMT-TU*CA
```

```
* = CCCH2NH-Boc
(N-t-butyloxycarbonylpropargyl amine)
* = CCCH2NHCOBP(Me)Ru(BP)2(PF6)2
(bis(2,2'-bipyridine)(4'-methyl-2,2'-bipyridine-4-
carbonylpropargylamine) ruthenium(II)
bis(hexafluorophosphate)
* = CCCH2NHCO(CH2)5NHCO(CH2)5NHCO-biotin
(6-(6-biotinoylaminohexanoyl)aminohexanoyl)
propargyl amine
* = CCCH2NHCOCF3
(N-trifluoracetylpropargyl amine)
* = CCCH2NHCOBP(Me)Ru(BP)2(PF6)2
* = CCCH2NHCOBP(Me)Os(BP)2(PF6)2
(bis(2,2'-bipyridine)(4'-methyl-2,2'-bipyridine-4-
carbonylpropargylamine) osmium(II)
bis(hexafluorophosphate)
* = CCCH2NHCOBP(Me)Ru(BP)2(PF6)2
* = CCCH2NHCOBP(Me)Os(BP)2(PF6)2
* = CCCH2NHCO(CH2)5NHCO(CH2)5NHCO-biotin
* = CCCH2NHCO(CH2)5NHCO(CH2)5NHCO-biotin
* = CCCH2NHCOBP(Me)Ru(BP)2(PF6)2
```

EXAMPLE 29

5'-O-mesyl-2'-deoxythymidine
(Compound 2 of FIG. 7)

2'-deoxythymidine 1 (2.90 g, 12.0 mmol) was dissolved in 10 mL dry pyridine and cooled to −10° C. Next, mesyl chloride (14 mmol) was added dropwise with magnetic stirring and over a period of 20 minutes. The reaction mixture was then held at 0° for 12 h. The next day, 10 mL methanol was added to quench the reaction and the solvents were evaporated via high vacuum. The resulting crude product was checked by TLC and purified by column chromatagraphy. A white powdered solid 2 was obtained (2.95 g, 77% yield). 1H NMR DMSO, d 1.78 (s, 3H, 5-methyl), 2.08–2.22 (m, 2H, C2'), 3.22 (s, 3H, mesyl), 3.98 (q, 1H, C4'), 4.28 (m, 1H, C3'), 4.40 (m, 2H, C5'), 5.50 (s, 1H, 3'-OH), 6.22 (t 1H, C1'), 7.48 (s, 1H, $C_6$), 11.25 (s, 1H, N3). MS(FAB): calculated MW=320, found M+H 321.

EXAMPLE 30

5'-azido-2'-deoxythymidine
(Compound 3 of FIG. 7)

A solution of 2 (1.84 g, 5.75 mmol) in 15 mL of DMF containing lithium azide (1.60 g, 32.6 mmol) was stirred at 90° C. under nitrogen. After three hours, the reaction was stopped and mixture was cooled to room temperature, and then poured into 600 mL ice-water. The resulting white precipitate was obtained via filtration. Column chromatagraphy yielded 3 (1.12 g, 73% yield). 1H NMR DMSO, d 1.78 (s, 3H, 5-methyl), 2.08–2.22 (m, 2H, $C_2$'), 3.57 (d, 2H, $C_5$'), 3.85 (q, 1H, C4'), 4.20 (m, 1H, C3'), 5.50 (s, 1H, 3'-OH), 6.22 (t, 1H, C1'), 7.48 (s, 1H, C6), 11.25 (s, 1H, N3).

EXAMPLE 31

5'-amino-2'-deoxythymidine
(Compound 4 of FIG. 7)

5'-azido-2'-deoxythymidine, (Compound 3 of FIG. 7), (1.12 g, 4.2 mmol) and triphenylphosphine (1.74 g, 6.7 mmol) were dissolved in 30 mL dioxane and stirred for three hours. A concentrated ammonia solution (15 mL) was then added to the reaction mixture. The reaction was determined to be complete by TLC 12 hours later. The solvents were removed, and the resulting residue was partially dissolved in ether/petrolum ether (1:1). A solid was obtained via filtration, and was further purified by column chromatography to yield 4 (0.73 g, 72% yield). 1H NMR DMSO, d 1.78 (s, 3H, 5-methyl), 2.08–2.18 (m, 2H, C2'), 2.75 (s, 2H, amine), 3.37 (s, 2H C5'), 3.75 (q, 1H, C4'), 4.20 (m, 1H, C3'), 5.20 (s, 1H, 3'-OH), 6.20 (t, 1H, C1'), 7.68 (s, 1H, C6). MS (FAB): calculated MW=241, found M+H 242; MS (FAB-HR) $C_{10}H_{15}N_3O_4$.

EXAMPLE 32

4'-Methyl-2,2'-bipyridine-4-carboxylic acid was synthesized following the procedure described by Peck, B. M.; Ross, G. T.; Edwards, S. W.; Meyer, G. I.; Meyer, T. J.; Erickson, B. W. Synthesis of Redox Derivatives of Lysine and Related Peptides Containing Phenothiezine or tris(2,2' bipyridine) ruthenium(II) Int. J. Pept. and Protein Res. 1991, 38, 114–123 with a yield of 77%; FAB-MS calculated $C_{12}H_{10}N_2O_2$ 214, found [M+H] 215; 1H NMR (DMSO-d6) d 2.5 (s, 3H, $CH_3$); 7.15-9 (m, 6H, py).

EXAMPLE 33 bis(2,2'-bipyridine)(4'-methyl-2,2'-bipyridine-4-carboxylic acid) ruthenium(II) bis (hexafluorophosphate)

A solution of cis-dichlorobisbipyridine Ru(II) (0.54 g, 1.0 mmol) in 50 mL ethanol was stirred under $N_2$ for 10 minutes. Next, 4-methyl-2,2'-bipyridine-4'-carboxylic acid (0.26 g, 1/2 mmol) was added to the solution and the reaction was refluxed for five hours. The reaction was stopped and the mixture was cooled to 25° C. before adding a saturated aqueous solution of $NH_4PF_6^-$. The red precipitate was collected by filtration and yielded 0.87 g of product (91% yield).

EXAMPLE 34

5'-[bis(2,2'-bipyridine)(4'-methyl-2,2'-bipyridine-4-carboxylic acid) ruthenium(II) bis (hexafluorophosphate) 2'-deoxythymidine
(Compound 5 of FIG. 7)

A solution of (4-methyl, 4'-carboxylic acid) bipyridine bisbipyridine ruthenium (0.20 g, 0.21 mmol) and carbonyl diimidazole CDI (0.06 g, 0.38 mmol) in 2 mL dry DMF was stirred under nitrogen at 25° C. for an hour. The mixture was then diluted with 3.5 mL dry THF and then the LH-20 resin (0.09 g) was added to quench excess CDI. An hour later, LH-20 was removed and 4 (0.05 g, 0.22 mmol) was added to the reaction mixture. After stirring for 12 h, the reaction was stopped and the solvents removed. Column chromatography yielded a red solid (compound 5) (0.19 g, 80% yield). MS(FAB) calculated MW=1 140, found (MW-$PF_6$)+H 996. MS(HR-FAB): C42 H39 O5 N9 F6 P Ru

EXAMPLE 35

5'-[bis(2,2'-bipyridine)(4'-methyl-2,2'-bipyridine-4-carboxylic acid) ruthenium(II) bis (hexafluorophosphate)] 3'-phosphoramidite 2'-deoxythymidine (Compound 6 of FIG. 7)

2-cyanoethylchloro-diisopropylphosphoramidite (50 μL, 0.22 mmol) was added to a solution of compound 5 of FIG. 7 (0.193 g, 0.17 mmol) in dry diisopropylethyl amine (0.1 mL) and dry $CH_3CN$ (8.5 mL). The reaction mixture proceeded under nitrogen for two hours. Solvents were then removed and residue was rinsed with hexane. The red solid was then checked by 31P NMR, $CDCl_3$: d 150 and 148 ppm.

EXAMPLE 36

Oligonucleotide Syntheses

The oligonucleotide syntheses were performed on a commercial ABI 395 DNA/RNA synthesizer from the 3' to 5' end using standard automated DNA synthesis protocols as shown in FIG. 8 (0.2 μmol scale). A 0.1 M solution of 5'-DMT-3'-cyanoethyl-N,N'-diisopropyl phosphoramidite-2'-deoxy-5-iodouridine in dry acetonitrile was prepared and installed on the DNA synthesizer in a standard reagent bottle. Normal solid-phase oligonucleotide synthesis was performed. In the last step, the ruthenium-modified thymidine phosphoramidite was introduced and allowed to react with the oligonucleotide for 15 minutes. The $Ru(bpy)_3^{2+}$ labeled oligonucleotide was cleaved from the column and deprotected. The ruthenium-modified oligonucleotided exhibited one peak in an HPLC trace, with retention times greater than the corresponding unmodified oligonucleotide. Electrospray mass spectrometry of the metallo-oligonucleotide confirmed formation [e.g., Compound 7, Electrospray (calculated 4545; found +2 (2275.33 and +3 (1516.79) ion stated; Compound 10 calculated (5789 found +2 (2896.77) and +3 (1931.34) ion states]. Collection and analysis of the trityl fractions during automated synthesis showed efficient phosphoramidite coupling throughout the procedure, with both the standard pyrimidine and purine nucleosides (>95%). The coupling of Compound 6 of FIG. 8 to the oligonucleotide in good yield (50%).

EXAMPLE 37

HPLC Purification of the Oligonucleotides

HPLC purification of the modified oligonucleotides was accomplished on a Ranin HPLC instrument. Reverse phase chromatography was performed on a C 18 column (25 cm×4.6 mm) with acetonitrile (ACN) and 0.1 M triethylamine acetate (TEAA) as eluting solvents. A flow rate of 1 mL/min was used and the concentration of ACN was increased from 5% to 50% over 35 minutes. The retention times of the modified oligonucleotides were well separated from the unmodified oligonucleotide products (>2 minutes in retention time).

EXAMPLE 38

Melting Curves

The stability of the duplex formed between the two complimentary oligonucleotides was determined by analyzing the melting curve profile as a function of temperature. Briefly stated, 2 mM stock solutions of the separate oligonucleotides were prepared and diluted to a working solution of 0.5 absorbance units. Next the two solutions are combined and the solution containing the complimentary oligomers was heated to 90° C. for 5 minutes. The solution was then allowed to cool to room temperature over 3 hrs. After cooling, the thermal denaturation experiment was performed using the following parameters on a HP UV-VIS: a) monitoring wavelength, 260 nm, b) temperature range, 20 –75° C., c) temperature step, 0.1° C., d) averaging time constant, 15 s, e) rate of change for the temperature step, 1° C./minute, and f) equilibrium time, 30 s.

EXAMPLE 39

S$^2$FTIR

The transient data reported here were measured on a step-scan modified Bruker IFS88 spectrometer with a standard globar source and dry air purge. The sample was dissolved in $CD_3CN$ to give an IR absorbance between 0.125 and 0.5 in a 250 mm pathlength cell for the amide bond analyzed. Samples were deoxygenated by sparging with argon for 60 minutes and were loaded into a $CaF_2$-window cell by syringe under argon. Data collection and analysis was performed as previously reported. Khan, S. I.; Beilstein, A. E.; Smith, G. D.; Sykora, M.; Grinstaff, M. W. Synthesis and Excited-State Properties of a Novel Ruthenium Nucleoside Inorg. Chem. 1999, 38, 2411–2415.

EXAMPLE 40

Emission Spectra

Emission spectra were recorded on a Spex Fluorolog-2 emission spectrometer equipped with a 450 W Xe lamp and cooled Hammamatsu $R_{928}$ photomultiplier. The recorded emission spectra were corrected for spectrometer response. The calibration curve was obtained using NIST calibrated standard lamp (Optronics Laboratories, Inc. Model 220M), controlled with a precision current source at 6.5 W (Optronics Laboratories, Inc. Model 65) by following the procedure recommended by manufacturer. The spectra were obtained in buffer at room temperature in a 1 cm quartz cell using right angle observation of emitted light.

EXAMPLE 41

Lifetimes

A Laser Photonics LN1000 Nitrogen Laser-LN102 dye laser (coumarin 460 dye, Exciton) was used as the irradiation source. The emission was monitored at a right angle using a Macpherson 272 monochromator and Hammamatsu $R_{666}$-10 PMT. The signal was processed by a LeCroy 7200A transient digitizer interfaced with an IBM-PC. The excitation wavelength was 460 nm and the monitoring wavelength was 640 nm. Power at the sample was 41 µJ/pulse as measured by a Molectron J3-09 power meter. The measured instrument lifetime response is 10 ns (FWHM). The acquired emission decay curves were analyzed by locally written software based on the Marquardt algorithm.

EXAMPLE 42

Electron Transfer

The ruthenium-uridine described herein is a suitable chromophore for reductive quenching studies since it is photochemically stable, inert to ligand substitution reactions, possesses an energetic excited state (0.84 eV), and a long lifetime in fluid solution. Moreover, the excited-state electron is localized on the bipyridine attached to the uridine. The electron-transfer quencher, phenothiazine is known to be a very efficient electron donor for quenching *Ru(bpy)$_3$$^{2+}$. The biomolecular electron-transfer reaction between compounds 4 and 7 of FIGS. 1A–1B was studied in solution by varying the quencher concentration. Stern-Volmer analysis yielded a quenching rate constant (kq) of $1.3 \times 10^9$ $M^{-1}$ $s^{-1}$. Based on the reduction potential of PTZ+/0 (0.76 eV), the driving force for this electron-transfer reaction was estimated to be approximately 0.1 eV.

In this DNA-mediated electron-transfer system, the electron donor and acceptor were covalently attached to different oligonucleotide strands and separated by about 30 Å. First, the complimentary duplex containing only the ruthenium acceptor (5'-TCA ACA GU*T TGT AGC A-3'; 5'-TGC TAC AAA CTG TTG A-3') was synthesized (U*=Ru(diimine)$_3$$^{2+}$ linked uridine). The emission maximum for this ruthenium-labeled oligonucleotide duplex was centered at 660 nm and the emission lifetime was measured to be 540 ns at 20° C. in phosphate buffer (monitoring at 640 nm after 455 nm pulse excitation). Next, phenothiazine (PTZ) was attached to the 5'-terminal of the complimentary sequence of the ruthenium labeled oligonucleotide (5'-TCA ACA GU*T TGT AGC A-3'; 5'-PTZ-TGC TAC AAA CTG TTG A-3'). Reductive quenching of the excited state was observed, and the rate constant was determined to be $2.6 \times 10^5$ $s^{-1}$. The lifetime and electron-transfer rates were measured using a Laser Photonics LN1000 Nitrogen Laser-LN102 dye laser (coumarin 460 dye). The emission was monitored at right angle with a Macpherson 272 monochromator and Hammamatsu $R_{666}$-10 PMT at 22° C. The signal was processed by a LeCroy 7200A transient digitizer interfaced with an IBM-PC. The excitation wavelength was 455 nm and the monitoring wavelength was 640 nm. Power at the sample was 60 W/pulse.mm$^3$ as measured by a Molectron J3-09 power meter. The measured instrument response function is 10 ns (FWHM). The acquired emission decay curves were analyzed by a locally written software based on the Marquardt algorithm. The data were fit to a single exponential. The residuals between the experimental and fitted curves were less than 2%. The electron-transfer rate constant was determined using the following equation: $k = 1/t - 1/t_0$. Over the temperature range of 5 to 30° C., the rate constant increased slightly from 2.5 to $2.8 \times 10^5$ $s^{-1}$.

All references cited herein, including the following, are incorporated herein by reference in their entirety. Palladium (0) Catalyzed Modification of Oligonucleotides during Automated Solid-Phase Synthesis." Shoeb I. Khan and Mark W. Grinstaff. J. Am. Chem. Soc. 1999, 121, 4704–4705. "Automated Solid-Phase Synthesis of Site Specifically Labeled Ruthenium-Oligonucleotides." Shoeb I. Khan, Amy E. Beilstein, and Mark W. Grinstaff. Inorg. Chem. 1999, 38, 418–419. "Synthesis and Excited-State Properties of a Novel Ruthenium Nucleoside: Ru(bpy)$_2$(5-bpy-2'-deoxyuridine)$^{2+}$." Shoeb I. Khan, Amy E. Beilstein, Gregory D. Smith, Milan Sykora, and Mark W. Grinstaff. Inorg. Chem. 1999, 38, 2411–2415. "The Alkylation of Iodouridine by a Heterogeneous Palladium Catalyst." Shoeb I. Khan and Mark W. Grinstaff. J. Org. Chem. 1999, 64, 1077–1078.

We claim:

1. An improved method of synthesizing a labeled oligonucleotide comprising:
   attaching a nucleoside of the oligonucleotide to be synthesized to a solid support through a labile linker arm;
   said nucleoside containing a removable protecting group attached to a 5' hyroxyl of a sugar group of said nucleoside;
   removing said protecting group;
   adding a further nucleoside containing a linker arm and a protecting group to said solid support under conditions where said further nucleoside is coupled to said 5' hydroxyl of said sugar group through said linker arm;
   optionally capping any uncoupled nucleoside;
   removing the protecting group of said further nucleoside;
   repeating the above with further nucleoside derivatives wherein at least one of said further nucleoside contains a detectable label, until a desired oligonucleolide is formed; and
   cleaving said oligonucleotide from said solid support;
   wherein the improvement comprises adding at least one dimethoxytrityl, phosphorarridite halonucleoside derivative in place of one of said at least one nucleoside containing a detectable label, wherein said halonucleoside is selected from the group consisting of a C5-halo-pyrimidine, a C8-halo-puine and a C7-halo-7-deazapurine; and
   labeling said halonucleoside derivative with a detectable label in place of said halogen during or subsequent to formation of said oligonucleotide.

2. The method of claim 1 wherein said cleaving comprising adding concentrated ammonium hydroxide.

3. The method of claim 1, further comprising treating said cleaved oligonucleotide with heat or light to remove any protecting group.

4. An improved method of oligonucleotide synthesis comprising combining phosphoramidite nucleoside derivatives in combination with a solid support wherein the improvement comprises adding at least one phosphoramidite halonucleoside during the synthesis and subsequently labeling said halonucleoside with a marker in a metal catalyzed reaction in place of said halogen to form a labeled nucleoside, wherein said halonucleoside is selected from the group consisting of a C5-halo-pyrimidine, a C8-halopurine and a C7-halo7-deazapurine.

5. The improved method of claim 4 wherein said metal is palladium.

6. The improved method of claim 4 wherein said halonucleoside is selected from the group consisting of fluorouridine, fluoroadenosine, fluoroguanosine, fluorocytidine, fluorothymidine, chlorouridine, chloroadenosine, chloroguanosine, chlorocytidine, chlorothymidine, iodouridine, iodoadenosine, iodoguanosine, iodocytidine, iodothymidine, bromouridine, bromoadenosine, bromoguanosine, bromocytidine and bromothymidine.

7. The improved method of claim 4 wherein said oligonucleotide synthesis progresses in the 3' to 5' or the 5' to 3' direction.

8. The improved method of claim 4 wherein the marker is a metal-containing alkene or alkyne derivative.

9. The improved method of claim 4, wherein said labeled nucleoside comprises a detectable marker which is a metal complex containing at least one of a $M(diimine)_x^{y+}$ complex, $M(terpyridine)_x^{y+}$ complex or a metallocene wherein M is a transition metal, said diimine is selected from a bipyridine, phenanthroline or terpyridine derivative; x is 1, 2, or 3 and y is 0, 1, 2, 3, or 4, said bipyridine, phenanthroline, terpyridine and metallocene being optionally substituted by any one of alkyl, alkene, alkyne, aryl, alkylaryl, and carboxyalkyl, amide, ester or ether.

10. The improved method of claim 9, wherein said detectable marker contains at least one of a $M(diimine)_2$ $(diimine)^{2+}$ complex wherein M is a metal selected from $Fe^{+2}$, $Ru^{+2}$, $Os^{+2}$, $Co^{+2}$, $Rh^{+2}$, and $Cr^{+2}$, or a $M(diimine)_2$ $(diimine)^{3+}$ complex wherein M is a metal selected from $Fe^{+3}$, $Ru^{+3}$, $OS^{+3}$, $Co^{+3}$, $Rh^{+3}$, and $Cr^{+3}$, or a $M(terpyridine)_2^{3+}$ complex wherein M is a selected from $Fe^{+3}$, $Ru^{+3}$, $Os^{+3}$, $Co^{+3}$, $Rh^{+3}$, and $Cr^{+3}$, or a $M(diimine)_2^{2+}$ complex wherein M is a metal selected from $Fe^{+2}$, $Ru^{+2}$, $Os^{+2}$, $Co^{+2}$, $Rh^{+2}$, and $Cr^{+2}$.

11. The improved method of claim 1, wherein said nucleoside comprises a sugar selected from the group consisting of a ribose, a deoxyribose and a dideoxyribose.

12. The improved method of claim 4, wherein said nucleoside comprises a sugar selected from the group consisting of a ribose, a deoxyribose and a dideoxyribose.

13. The improved method of claim 1, wherein said nucleoside further comprises a dimethoxytritylchloride, α-methyl-6-nitropipronyloxy carbonyl or 2-cyanoethyl N,N'-diisopropylcholoro phosphoramidite derivative.

14. The improved method of claim 4, wherein said nucleoside further comprises a dimethoxytritylchloride, α-methyl-6-nitropipronyloxy carbonyl or 2-cyanoethyl N,N'-diisopropylcholoro phosphoramidite derivative.

15. The improved method of claim 1, wherein said nucleoside further comprises a compound of the following structure:

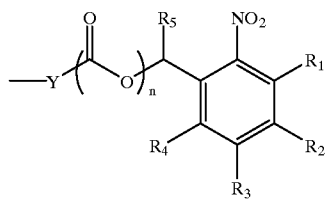

wherein $R_1$, $R_2$, $R_3$, and $R_4$ independently are a hydrogen atom, a lower alkyl, aryl, benzyl, halogen, hydroxyl, alkoxyl, thio, thioether, amino, nitro, carboxyl, formate, foramino or phosphido group, or adjacent substituents $R_1$–$R_4$ are substituted oxygen groups that together form a cyclic acetal or ketal; $R_5$ is hydrogen, alkoxyl, alkyl, halo, aryl or alkenyl group, n=0, 1, 2 or 3; and Y is a hydroxyl group of the nucleoside.

16. The improved method of claim 4, wherein said nucleoside further comprises a compound of the following structure:

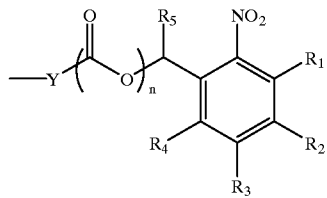

wherein $R_1$, $R_2$, $R_3$, and $R_4$ independently are a hydrogen atom, a lower alkyl, aryl, benzyl, halogen, hydroxyl, alkoxyl. thio, thioether, amino, nitro, carboxyl, formate, for amino or phosphido group, or adjacent substituents $R_1$–$R_4$ are substituted oxygen groups that together form a cyclic acetal or ketal; $R_5$ is hydrogen, alkoxyl, alkyl, halo, aryl or alkenyl group, n=0, 1, 2 or 3; and Y is a hydroxyl group of the nucleoside.

17. The improved method of claim 1, wherein said nucleoside contains a uricil, adenine, thymine, cylosine, guanine or natural or synthetic analogs thereof.

18. The improved method of claim 4, wherein said nucleoside contains a uricil, adenine, thymine, cytosine, guanine or natural or synthetic analogs thereof.

19. The improved method according to claim 9, wherein said detectable marker is selected from a bis(2,2'-bipyridine) (4'-methyl-2,2'-bipyridine-4-carbonyl propargyl amine) ruthenium (II) substituent, a ferrocene substituent; and a bis(2,2'-bipyridine) (4'-methyl-2,2'-bipyridine-4-carbonyl propargyl amine) osmium (II) substituent.

20. The improved method according to claim 9, wherein said diimine ligands around said metal are all the same.

21. The improved method according to claim 9, wherein at least two of said diimine ligands around said metal are not the same.

* * * * *

SEQUENCE LISTING

<160> NUMBER OF SEQ ID NOS: 22

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence:
      SITE-SPECIFIC INCORPORATION OF PROBE TESTED
<221> NAME/KEY: variation
<222> LOCATION: (8)
<223> OTHER INFORMATION: RUTHENIUM-MODIFIED URIDINE

<400> SEQUENCE: 1
tcaacagutt gtagca                                              16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence:
      SITE-SPECIFIC INCORPORATION TEST SAMPLE
<221> NAME/KEY: variation
<222> LOCATION: (1)
<223> OTHER INFORMATION: RUTHENIUM-MODIFIED URIDINE

<400> SEQUENCE: 2
ucaacagttt gtagca                                              16

<210> SEQ ID NO 3
<211> LENGTH: 16
<212> TYPE: DNA
<213> ORGANISM: Artificial Sequence
<220> FEATURE:
<221> NAME/KEY: variation
<222> LOCATION: (12)
<223> OTHER INFORMATION: RUTHENIUM-MODIFIED URIDINE
<223> OTHER INFORMATION: Description of Artificial Sequence:
      SITE-SPECIFIC INCORPORATION TEST SAMPLE

<400> SEQUENCE: 3
tcaacagttt guagca                                              16

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence:
      SITE-SPECIFIC INCORPORATION CONTROL

<400> SEQUENCE: 4
tcaacagttt gtagca                                              16

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence:
      SITE-SPECIFIC INCORPORATION CONTROL

<400> SEQUENCE: 5
tgctacaaac tgttga                                              16

```
<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence:
      SITE-SPECIFIC INCORPORATION CONTROL

<400> SEQUENCE: 6
tcgtacaaac tgttga                                                      16

<210> SEQ ID NO 7
<211> LENGTH: 13
<212> TYPE: DNA
<213> ORGANISM: Artificial Sequence
<220> FEATURE:
<221> NAME/KEY: variation
<222> LOCATION: (1)
<223> OTHER INFORMATION: RUTHENIUM-MODIFIED THYMIDINE
<223> OTHER INFORMATION: Description of Artificial Sequence:
      SITE-SPECIFIC INCORPORATION TEST SAMPLE

<400> SEQUENCE: 7
ttcaacagtt tgt                                                         13

<210> SEQ ID NO 8
<211> LENGTH: 16
<212> TYPE: DNA
<213> ORGANISM: Artificial Sequence
<220> FEATURE:
<221> NAME/KEY: variation
<222> LOCATION: (1)
<223> OTHER INFORMATION: RUTHENIUM-MODIFIED THYMIDINE
<223> OTHER INFORMATION: Description of Artificial Sequence:
      SITE-SPECIFIC INCORPORATION TEST SAMPLE

<400> SEQUENCE: 8
tcaacagttt gtagca                                                      16

<210> SEQ ID NO 9
<211> LENGTH: 16
<212> TYPE: DNA
<213> ORGANISM: Artificial Sequence
<220> FEATURE:
<221> NAME/KEY: variation
<222> LOCATION: (1)
<223> OTHER INFORMATION: RUTHENIUM-MODIFIED THYMIDINE
<223> OTHER INFORMATION: Description of Artificial Sequence:
      SITE-SPECIFIC INCORPORATION TEST SAMPLE

<400> SEQUENCE: 9
tgctaccctc tgttga                                                      16

<210> SEQ ID NO 10
<211> LENGTH: 17
<212> TYPE: DNA
<213> ORGANISM: Artificial Sequence
<220> FEATURE:
<221> NAME/KEY: variation
<222> LOCATION: (1)
<223> OTHER INFORMATION: RUTHENIUM-MODIFIED THYMIDINE
<223> OTHER INFORMATION: Description of Artificial Sequence:
      SITE-SPECIFIC INCORPORATION TEST SAMPLE

<400> SEQUENCE: 10
ttcaacagtt tgtagca                                                     17

<210> SEQ ID NO 11
<211> LENGTH: 13
```

```
<212> TYPE: DNA
<213> ORGANISM: Artificial Sequence
<220> FEATURE:
<223> OTHER INFORMATION: Description of Artificial Sequence:
      SITE-SPECIFIC INCORPORATION TEST SAMPLE

<400> SEQUENCE: 11
ttcaacagtt tgt                                                        13

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence:
      SITE-SPECIFIC INCORPORATION TEST SAMPLE

<400> SEQUENCE: 12
tgctaccctc tgttga                                                     16

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:
      SITE-SPECIFIC INCORPORATION TEST SAMPLE

<400> SEQUENCE: 13
ttcaacagtt tgtagca                                                    17

<210> SEQ ID NO 14
<211> LENGTH: 13
<212> TYPE: DNA
<213> ORGANISM: Artificial Sequence
<220> FEATURE:
<223> OTHER INFORMATION: Description of Artificial Sequence:
      SITE-SPECIFIC INCORPORATION TEST SAMPLE

<400> SEQUENCE: 14
acaaactgtt gaa                                                        13

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence:
      SITE-SPECIFIC INCORPORATION TEST SAMPLE

<400> SEQUENCE: 15
tcaacagagg gtagca                                                     16

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence:
      SITE-SPECIFIC INCORPORATION TEST SAMPLE

<400> SEQUENCE: 16
tgctacaaac tgttgaa                                                    17

<210> SEQ ID NO 17
<211> LENGTH: 16
<212> TYPE: DNA
```

```
<213> ORGANISM: Artificial Sequence
<220> FEATURE:
<223> OTHER INFORMATION: Description of Artificial Sequence:
      SITE-SPECIFIC INCORPORATION TEST SAMPLE
<221> NAME/KEY: variation
<222> LOCATION: (12)
<223> OTHER INFORMATION: RUTHENIUM-MODIFIED URIDINE

<400> SEQUENCE: 17
tcaacagttt guagca                                                    16

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence:
      SITE-SPECIFIC INCORPORATION TEST SAMPLE
<221> NAME/KEY: variation
<222> LOCATION: (12)
<223> OTHER INFORMATION: OS-MODIFIED URIDINE

<400> SEQUENCE: 18
tcaacagttt guagca                                                    16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence:
      SITE-SPECIFIC INCORPORATION TEST SAMPLE
<221> NAME/KEY: variation
<222> LOCATION: (13)
<223> OTHER INFORMATION: Ru-MODIFIED URIDINE

<400> SEQUENCE: 19
tgctacaaac tgutga                                                    16

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence:
      SITE-SPECIFIC INCORPORATION TEST SAMPLE
<221> NAME/KEY: variation
<222> LOCATION: (13)
<223> OTHER INFORMATION: Os-MODIFIED URIDINE

<400> SEQUENCE: 20
tgctacaaac tgutga                                                    16

<210> SEQ ID NO 21
<211> LENGTH: 12
<212> TYPE: DNA
<213> ORGANISM: Artificial Sequence
<220> FEATURE:
<223> OTHER INFORMATION: Description of Artificial Sequence:
      SITE-SPECIFIC INCORPORATION TEST SAMPLE
<221> NAME/KEY: variation
<222> LOCATION: (10)
<223> OTHER INFORMATION: BIOTIN MODOFOED URIDINE

<400> SEQUENCE: 21
tacatcctau ct                                                        12

<210> SEQ ID NO 22
<211> LENGTH: 30
```

-continued

```
<212> TYPE: DNA
<213> ORGANISM: Artificial Sequence
<220> FEATURE:
<223> OTHER INFORMATION: Description of Artificial Sequence:
      SITE-SPECIFIC INCORPORATION TEST SAMPLE
<221> NAME/KEY: variation
<222> LOCATION: (28)
<223> OTHER INFORMATION: BIOTIN MODIFIED URIDINE

<400> SEQUENCE: 22
ggtcttattc accacaataa cctcagtuct                                      30
```